(12) United States Patent
Satterthwaite et al.

(10) Patent No.: US 10,251,752 B2
(45) Date of Patent: Apr. 9, 2019

(54) MODULAR FEMORAL PROSTHESIS SYSTEM FOR HIP ARTHROPLASTY

(71) Applicant: DePuy Synthes Products, Inc., Raynham, MA (US)

(72) Inventors: Rodney E. Satterthwaite, Huntington, IN (US); Jeffrey A. McAnelly, Columbia City, IN (US); Sean H. Kerr, Oreland, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/986,433

(22) Filed: Dec. 31, 2015

(65) Prior Publication Data

US 2017/0189190 A1   Jul. 6, 2017

(51) Int. Cl.
*A61F 2/36* (2006.01)
*A61F 2/30* (2006.01)
*A61F 2/46* (2006.01)

(52) U.S. Cl.
CPC ........ *A61F 2/3609* (2013.01); *A61F 2/30728* (2013.01); *A61F 2/367* (2013.01); *A61F 2/4607* (2013.01); *A61F 2002/305* (2013.01); *A61F 2002/30383* (2013.01); *A61F 2002/30433* (2013.01); *A61F 2002/30607* (2013.01); *A61F 2002/30729* (2013.01); *A61F 2002/3641* (2013.01); *A61F 2002/3652* (2013.01)

(58) Field of Classification Search
CPC ...... A61F 2002/3631; A61F 2002/3635; A61F 2002/3641; A61F 2002/3643; A61F 2002/3656
See application file for complete search history.

(56) References Cited

U.S. PATENT DOCUMENTS

| 4,012,796 | A   |   | 3/1977  | Weisman et al. |
|-----------|-----|---|---------|----------------|
| 4,770,660 | A   |   | 9/1988  | Averill et al. |
| 4,827,919 | A   |   | 5/1989  | Barbarito |
| 5,116,377 | A   |   | 5/1992  | Skripitz |
| 5,201,769 | A   | * | 4/1993  | Schutzer ............... A61F 2/3609 623/23.22 |
| 5,376,124 | A   | * | 12/1994 | Gustke ................ A61F 2/30724 623/23.28 |
| 5,766,262 | A   |   | 6/1998  | Mikhail et al. |
| 7,261,741 | B2  |   | 8/2007  | Weissman et al. |

(Continued)

FOREIGN PATENT DOCUMENTS

| EP | 216489 B1   | 1/1992 |
|----|-------------|--------|
| FR | 2863866 A1  | 6/2005 |

OTHER PUBLICATIONS

European Search Report for European Patent Application No. 16203841.8-1664, May 19, 2017, 9 pages.

*Primary Examiner* — Bruce E Snow
(74) *Attorney, Agent, or Firm* — Barnes & Thornburg LLP

(57) ABSTRACT

A modular femoral prosthesis system for an orthopedic hip implant and method of use is disclosed. The prosthesis system includes a femoral stem component and a plurality of collar components configured to be selectively coupled to the stem component in a fixed position adjacent to a neck of the stem component. Each of the collar components includes a base and is configured to secure an assembled femoral prosthesis to a patient's surgically prepared femur to provide stability for the assembled femoral prosthesis.

16 Claims, 19 Drawing Sheets

(56) References Cited

U.S. PATENT DOCUMENTS

| | | |
|---|---|---|
| 8,530,560 B2 | 9/2013 | Kerr et al. |
| 2003/0109933 A1 | 6/2003 | Weissman et al. |
| 2007/0067042 A1 | 3/2007 | Weissman |
| 2009/0222091 A1 | 9/2009 | Morrissette et al. |
| 2012/0323339 A1 | 12/2012 | Olalde Graells et al. |

\* cited by examiner

MODULAR FEMORAL PROSTHESIS
SYSTEM FOR HIP ARTHROPLASTY

TECHNICAL FIELD

The present disclosure relates generally to customizable femoral components used in a total hip arthroplasty and more particularly to one or more collars that may be coupled to a femoral stem of a hip prosthesis.

BACKGROUND

Joint arthroplasty is a well-known surgical procedure by which a diseased and/or damaged natural joint is replaced by a prosthetic joint. For example, in a primary hip arthroplasty surgical procedure, a prosthetic hip replaces a patient's natural hip. In a revision hip arthroplasty surgical procedure, a revision prosthetic hip replaces an implanted primary hip prosthesis. A typical prosthetic hip includes a femoral component and an acetabular component. A typical femoral component includes a stem having a neck and an elongated body extending distally from the neck, and a femoral head configured to be positioned on the neck of the stem. The stem of the femoral component is secured to a patient's femur. A typical acetabular component includes an acetabular cup and a liner. The acetabular cup component is secured to the patient's coxal bone and is formed to receive and secure the femoral

SUMMARY

According to one aspect of the disclosure, a modular femoral prosthesis system includes a stem component configured to be received in a proximal end of a patient's surgically prepared femur, the stem comprising a neck, an elongated body extending distally from the neck, and a trunnion configured to receive a femoral head component extending medially and proximally from the neck, and a plurality of collar components configured to be selectively coupled to the stem component in a fixed position adjacent to the neck of the stem component. Each of the plurality of collar components includes a base having an inferior surface configured to contact a surgically prepared proximal surface of the patient's femur. The plurality of collar components including a first collar component having the base, the base of the first collar component having a platform and a pair of arms extending away from a lateral end of the platform, and a second collar component including the base and a flange extending away from a lateral end of the base, the flange being configured to secure the second collar component in a fixed position relative to a trochanter of the patient.

In some embodiments, each collar component of the modular femoral prosthesis system is made of a material different than the stem component. The stem component is made of a metallic material and each collar component is made of a biocompatible polymeric material. The biocompatible polymeric material is polyether ether ketone (PEEK).

In some embodiments, the trunnion defines a longitudinal axis that extends through the neck of the stem component, the stem component further comprises a shoulder positioned between the elongated body and the neck, and each collar component is configured to be coupled to the shoulder such that the inferior surface of the base of each collar component extends transverse to the longitudinal axis defined by the trunnion. The shoulder includes an anterior surface, a posterior surface positioned opposite the anterior surface, and a medial surface positioned inferior of the neck and extending between the anterior and posterior surface, a groove defined in the anterior surface, the posterior surface, and the medial surface of the shoulder, the groove extending transverse to the longitudinal axis of the trunnion and being configured to receive the base of each collar component to secure each collar component to the stem component. When the first collar component is coupled to the stem component, each of the pair of arms is received into the groove defined in the shoulder of the stem component. When the second collar component is coupled to the stem component, an inner surface of the base is received into the groove defined in the shoulder of the stem component. The groove includes an anterior channel extending along the anterior surface of the shoulder and a posterior channel extending along the posterior surface of the shoulder, and each channel extends from a first open end defined in the medial surface of the shoulder to a second open end defined in a superior, lateral surface of the shoulder. A socket sized to receive an insertion tool is defined in the superior, lateral surface of the shoulder.

In some embodiments of the modular femoral prosthesis system, each collar component is configured to be coupled to the stem component via a press-fit. In yet other embodiments, the modular femoral prosthesis system also includes a fastener configured to couple each collar component to the stem component. In some embodiments, the platform of the first collar component defines a maximum anterior-posterior width, and the pair of arms of the first collar component defines a maximum anterior-posterior width that is less than the maximum anterior-posterior width of the platform. In some embodiments, the platform of the first collar component includes a curved outer surface that extends from an inferior surface to a superior surface of the first collar component, the curved outer surface extending from a first end connected to an anterior arm of the pair of arms to a second end connected to a posterior arm of the pair of arms.

According to another aspect, an orthopaedic femoral prosthesis includes a femoral stem component configured to be received in a proximal end of a patient's surgically prepared femur, the stem comprising a neck, an elongated body extending distally from the neck, and a trunnion configured to receive a femoral head component extending medially and proximally from the neck, and a collar component configured to be coupled to the stem component in a fixed position relative to the stem component. The collar component including a base and a flange, the base having a superior surface extending between a medial end of the base and a lateral end of the base, an inferior surface positioned opposite the superior surface, and an inner wall extending between a first opening formed in the superior surface and a second opening formed in the inferior surface to define a slot sized to receive the stem component. The flange extends away from the lateral end of the base and forms a non-orthogonal angle with the superior surface of the base, and the flange is configured to couple the stem component in a fixed position relative to the patient's trochanter.

In some embodiments, the flange of the collar component extends superiorly away from the elongated body of the stem when the collar component coupled to the stem component. In some embodiments, the trunnion defines a longitudinal axis that extends through the neck of the stem component, and the collar component is configured to be coupled to the stem component such that the inferior surface of the collar component extends transverse to the longitudinal axis of defined by the trunnion. In some embodiments, the stem component further comprises a groove formed therein, the groove being sized to receive the inner wall of the collar component when the collar component is secured to the stem component.

According to another aspect, a method for performing a hip arthroplasty is disclosed. The method including resecting a proximal end of a patient's femur to form a planar proximal surface, selecting a femoral stem component having a neck, an elongated body extending distally from the neck, and a trunnion configured to receive a femoral head component extending medially and proximally from the neck, inserting a broach through the planar proximal surface to define a passageway sized to receive the selected femoral stem component, selecting a collar component from a plurality of collar components, each collar component including an inferior surface configured to engage the planar proximal surface of the patient's femur, securing the selected collar component to the femoral stem component such that the inferior surface of the collar component extends transverse to a longitudinal axis of the trunnion of the femoral stem component, and implanting the femoral stem component in the patient's femur such that the inferior surface of the selected collar component engages with the planar proximal surface of the patient's femur.

In some embodiments, selecting the collar component further includes selecting a first collar component from the plurality of collar components, the first collar component including a base having the inferior surface configured to contact a surgically prepared proximal surface of the patient's femur, the base comprising a platform and a pair of arms extending away from a lateral end of the platform, the pair of arms cooperating to form a slot having an opening defined at a lateral end of the base, the slot being sized to receive the stem component, and securing the selected collar component to the femoral stem component further includes advancing the first collar component along a groove axis defined by a groove formed in the stem component, the groove axis extending transverse to the longitudinal axis defined by the trunnion. Advancing the first collar component further includes advancing the first collar component along the groove axis until the inner surface of the first collar component engages with the groove surface of the stem component.

In some embodiments, selecting the collar component further includes selecting a second collar component from the plurality of collar components, the second collar component including a base having the inferior surface configured to contact a surgically prepared proximal surface of the patient's femur and defining a slot sized to receive the stem component and a flange extending away from a lateral end of the base, the flange being configured to secure the second collar component in a fixed position relative to a trochanter of the patient. Securing the selected collar component to the femoral stem component further includes inserting a distal tip of the stem component into the slot of the second collar component, advancing the second collar component proximally along a body axis defined in the stem component, and engaging a groove surface that defines a groove formed in the stem component with the inner surface of the second collar component. The method may further include securing a trochanteric reattachment device to the patient's trochanter, the trochanteric reattachment device including a body and a plurality of cables, threading the plurality of cables through a plurality of passageways extending through the flange of the second collar component, and securing the threaded cables to the body of the trochanteric reattachment device.

BRIEF DESCRIPTION OF THE DRAWINGS

The detailed description particularly refers to the following figures, in which.

DETAILED DESCRIPTION OF THE DRAWINGS

Figure 1:
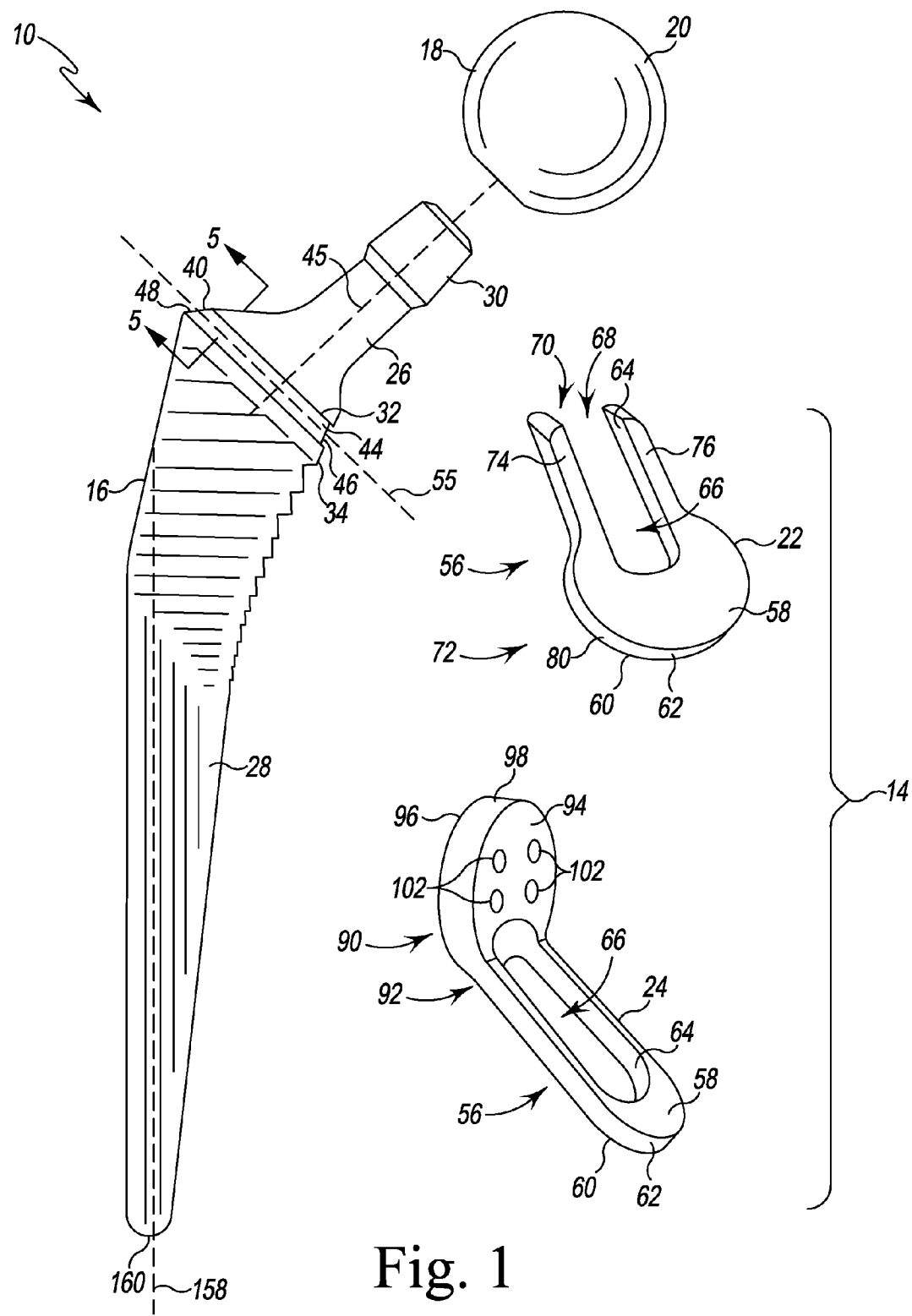
FIG. 1 is a perspective view of an embodiment of a femoral prosthesis system including a femoral stem component and a plurality of collar components for use with the stem component.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Referring to FIG. 1, a modular femoral prosthesis system 10 of a hip prosthesis is shown. The femoral prosthesis system 10 may be utilized to assemble a femoral prosthesis 12 customized to the needs of each patient. The femoral prosthesis system 10 includes a femoral stem component 16 that is configured to be implanted into the medullary canal of a patient's femur 130, a femoral head component 18 configured to be attached to the femoral stem component 16, and a plurality of modular collar components 14 configured to be separately and selectively secured to the femoral stem component 16. In use, an orthopaedic surgeon may assemble a femoral prosthesis 12 using the various components before implanting the assembled femoral prosthesis 12 in the patient's femur 130. For example, in some patients, the femoral prosthesis 12 may include only the stem component 16 and the femoral head component 18. For other patients, the orthopaedic surgeon may couple one of the collar components 14 to the stem component 16 to address specific additional needs of a patient, as described in greater detail below.

In the illustrative embodiment of FIG. 1, the collar components 14 include a stabilizing collar 22 and a trochanter collar 24 that may be selectively secured to the femoral stem component. As described in greater detail below, each collar component 14 is configured to be coupled to the stem component 16 in a fixed, immoveable position relative to the stem component 16. When the femoral prosthesis 12 is implanted, each collar component 14 is configured to engage the patient's femur 130 to provide additional stability for the femoral prosthesis 12. It should be appreciated that in other embodiments the plurality of collar components 14 of the femoral prosthesis system 10 may include additional collar configurations, including collar components of different sizes and shapes.

Although the system 10 may include a number of stem components 16 and femoral head components 18 of different sizes, the collar components 14 permit each stem component 16 to be customized based on the needs of a particular patient. In the illustrative embodiment, each stem component 16 may be used in one of three different configurations in a primary hip arthroplasty or in a revision hip arthroplasty. In that way, the number components in a surgical system may be reduced.

The illustrative stem component 16 is formed from an implantable metallic material such as, for example, stainless steel, cobalt chromium, or titanium. The femoral head component 18 is similarly formed from an implantable metallic material such as, for example, stainless steel, cobalt chromium, or titanium. In an illustrative embodiment, each collar component 14 is formed from a resorbable material that may be assimilated into the body over time. In the illustrative embodiment, each collar component 14 is made of a rigid polymer such as polyetheretherketone (PEEK). As a result, each collar component 14 is capable of providing more stability than a stem component 16 alone and is easier to manipulate in the event that a revision hip replacement is necessary. In other embodiments, one or more of the collar components 14 may be formed from a medical-grade metallic material such as stainless steel, cobalt chrome, or titanium, although other metals or alloys may be used.

As shown in FIG. 1, the femoral head component 18 includes a substantially spherical outer surface 20, which is configured to engage a corresponding bearing surface of an acetabular prosthetic component (not shown). An acetabular prosthetic component generally includes an outer shell configured to engage the acetabulum of the patient and an inner bearing or liner coupled to the shell that is configured to engage the femoral head component 18 to form a ball and socket joint that approximates the natural hip joint.

As shown in FIG. 1, the stem component 16 includes a neck 26, an elongated body 28 configured to be received in a surgically-prepared cavity of the patient's femur 130, and a trunnion 30 extending superiorly and medially from the neck 26. A shoulder 32 connects the neck 26 to the elongated body 28. As described in greater detail below, the shoulder 32 is configured to be secured to one of the collar components 14.

The elongated body 28 extends distally from the shoulder 32 to a distal tip 160. In the illustrative embodiment, the elongated body 28 is shaped to engage the patient's bone via a press-fit to secure the stem component 16 to the patient's femur. In other embodiments, the elongated body 28 may be secured via other attachment means such as, for example, bone cement.

The trunnion 30 is shaped to be received in a matching bore (not shown) of the femoral head component 18. In the illustrative embodiment, the bore and the trunnion 30 are tapered such that the femoral head component 18 may be secured to the stem component 16 via a Morse taper locking connection. In other embodiments, the trunnion 30 and the surface lining the bore of the femoral head component 18 may be threaded. As shown in FIG. 1, the trunnion 30 defines a longitudinal axis 45 that extends through its proximal end surface.

The shoulder 32 of the stem component 16 includes a medial surface 34 that is positioned inferior of the neck 26 and the trunnion 30, an anterior surface 36, and a posterior surface 38 positioned opposite the anterior surface 36. In the illustrative embodiment, the medial surface 34 connects the surfaces 36, 38. As shown in FIG. 1, the shoulder 32 also includes a superior, lateral surface 40 that extends between the surfaces 36, 38. In the illustrative embodiment, a socket 42 is defined in the lateral surface 40. The socket 42 is sized to receive an insertion tool (not shown), which may be used to implant the stem component 16 in the patient's femur 130.

As described above, the shoulder 32 is configured to be secured to one of the collar components 14. In the illustrative embodiment, the stem component 16 includes a groove 44 that is sized to receive portions of each collar component 14 to secure the collar component 14 to the stem component 16 via a press-fit connection. In other embodiments, other fastening means may be used to secure the collar component 14 to the stem component 16, including the exemplary methods described below in regard to FIGS. 20-21. For example, a collar component may be coupled to the femoral stem component via a press-fit, bio-compatible medical grade epoxy, medical grade cement, a fastener, a snap fit mechanism, or may be molded to the femoral stem component.

Figure 5:
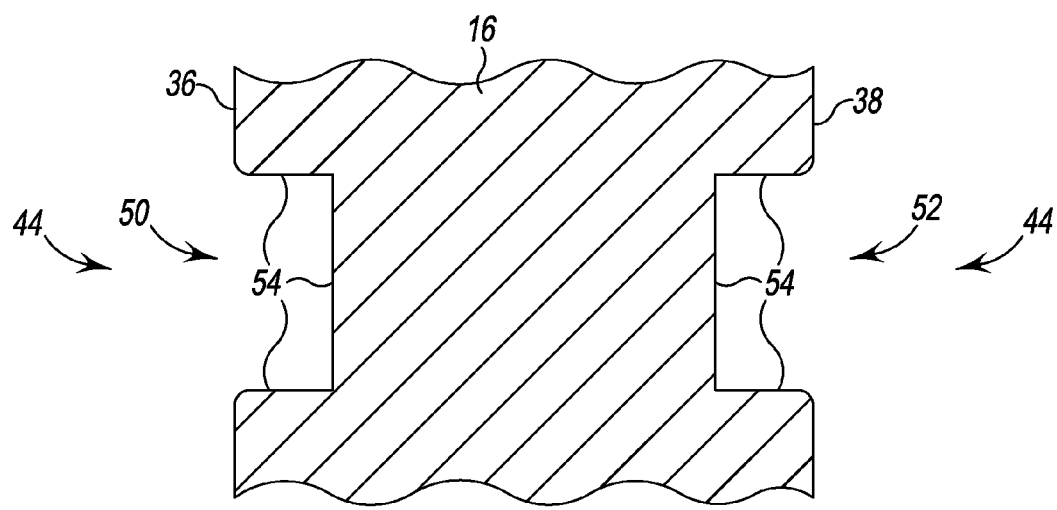
FIG. 5 is a cross-sectional view of the stem component of FIG. 1 taken along the line 5-5 in FIG. 1.

As shown in FIGS. 1 and 5, the groove 44 includes a pair of channels 50, 52 that are defined in the anterior surface 36 and the posterior surface 38, respectively, of the shoulder 32. The channels 50, 52 extend from open ends 46 defined in the medial surface 34 to open ends 48 defined in the superior, lateral surface 40. Each channel 50, 52 extends along a longitudinal axis 55 extending transverse to the longitudinal axis 45 of the trunnion 30. In the illustrative embodiment, the longitudinal axis 55 of each channel 50, 52 extends orthogonal to the longitudinal axis 45. In other embodiments, the longitudinal axis of the channels extends at non-orthogonal angles relative to the longitudinal axis 45. As shown in FIG. 5, each channel 50, 52 is defined by base walls 54 that extend inwardly from openings defined the surfaces 36, 38. The channels 50, 52 illustratively have rectangular cross-sections, but it should be appreciated that in other embodiments cross-sections of other geometric shapes (e.g., curved) may be used. Additionally, as shown in FIG. 5, each channel 50, 52 extends along a straight axis 55; it should be appreciated that in other embodiments one or both of the channels 50, 52 may extend partially or wholly along a curved axis.

As described above and shown in FIG. 1, the system 10 includes a stabilizing collar 22 and a trochanter collar 24, which are configured to be selectively coupled to the stem component 16. In the illustrative embodiment, each of the collars 22, 24 is configured to engage a surgically prepared proximal surface 132 of the patient's femur 130 when the femoral prosthesis 12 is positioned in the patient's femur 130. In other embodiments, however, the trochanter collar 24 may not engage the surgically prepared proximal surface of the patient's femur 130 and may be configured to only engage a portion of the patient's trochanter 134.

In the illustrative embodiment, each of the collars 22, 24 includes a base 56 that is configured to engage with the stem component 16. The base 56 includes a superior surface 58, an inferior surface 60 positioned opposite the superior surface 58, and an outer surface 62 that defines an outer edge of the each collar and extends between the superior surface 58 and the inferior surface 60. The inferior surface 60 of each collar is configured to engage the surgically prepared proximal surface 132 of the patient's femur 130. Each base 56 also includes an inner wall 64 extending from the superior surface 58 to the inferior surface 60 to define a slot 66. In the illustrative embodiment, the inner wall 64 of each of the collars 22, 24 is configured to engage the base walls 54 defining the channels 50, 52 to secure the collar to the stem component 16 via a press-fit or an interference fit. Additionally, as shown in FIGS. 1-4, the base 56 of each illustrative collar component 14 is planar; it should be appreciated that in other embodiments the base 56 may be curved or partially curved.

Figure 2:
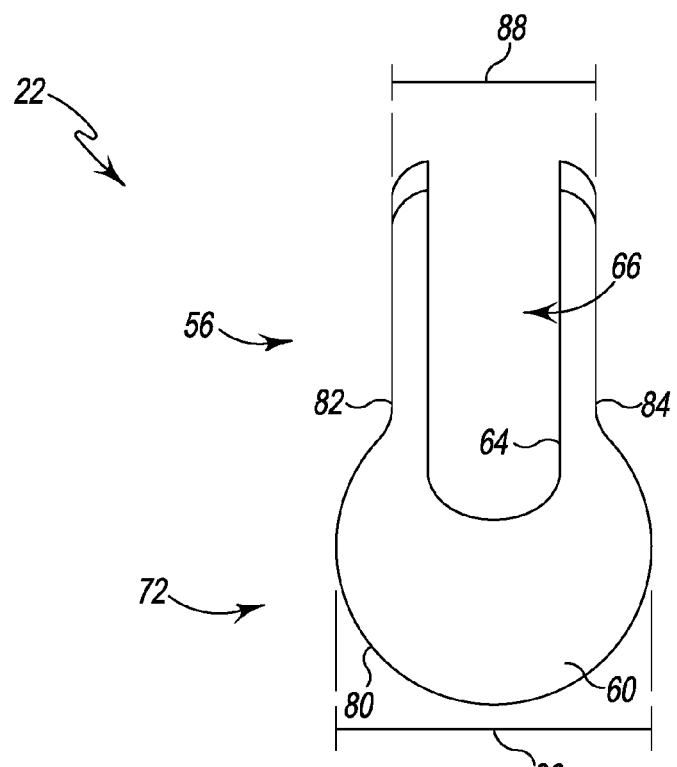
FIG. 2 is a bottom plan view of one of the collars of FIG. 1.

As shown in FIG. 2, the stabilizing collar 22 has an opening 68 formed at a lateral end 70 of its base 56 such that the slot 66 is an open-ended slot. In other embodiments, the slot of the stabilizing collar 22 may be a closed slot, similar to the slot of the trochanter collar 24 described below. The base 56 includes a platform 72 that is positioned opposite the opening 68 and a pair of arms 74, 76 that extend laterally from the platform 72 along the slot 66. The platform 72 includes a curved outer surface 80 that extends between the inferior surface 60 and the superior surface 58 of the base 56. The curved outer surface 80 extends from a first end 82 connected to an anterior arm 74 to a second end 84 connected to a posterior arm 76 of the pair of arms. In the illustrative embodiment, the platform 72 of the stabilizing collar 22 defines a maximum anterior-posterior width 86 that is greater than a maximum anterior-posterior width 88 defined by the pair of arms 74, 76 of the base 56. In other embodiments, the maximum anterior-posterior width 86 of the platform 72 is equal to or less than the maximum anterior-posterior width 88 of the pair of arms 74, 76.

Figure 3:
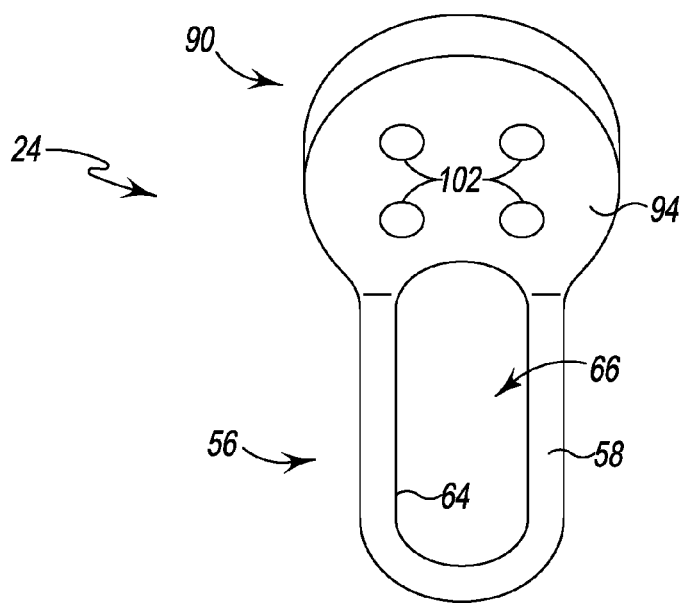
FIG. 3 is a top plan view of another of the collars of FIG. 1.
Figure 4:
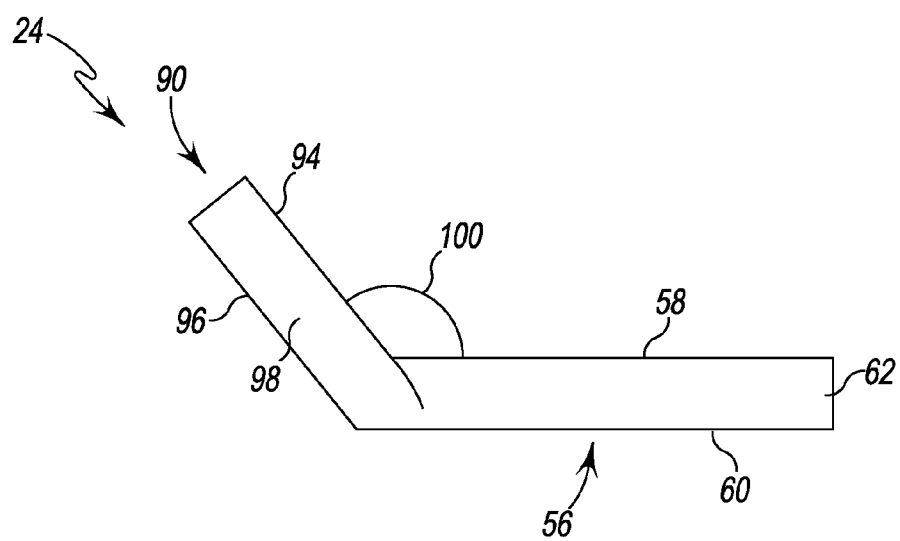
FIG. 4 is a side elevation view of the another collar of FIG. 3.

As shown in FIG. 3, the illustrative slot 66 of the trochanter collar 24 is surrounded by the inner wall 64 such that the slot 66 is a closed slot. The trochanter collar 24 includes the base 56 and a flange 90 extending away from a lateral end 92 of the base 56. The flange 90 of the trochanter collar 24 includes a medial surface 94, a lateral surface 96 positioned opposite the medial surface 94, and an outer surface 98 that connects the surfaces 94, 96. As shown in FIG. 4, the medial surface 94 extends away from the superior surface 58 of the base 56 and cooperates with the superior surface 58 to define an angle 100. In the illustrative embodiment, the angle 100 is a non-orthogonal angle relative to the superior surface 58 of the base 56. When the trochanter collar 24 is coupled to the stem component 16, the flange 90 extends superiorly away from elongated body 28 of the stem component 16 (see FIG. 10).

Returning to FIG. 3, the trochanter collar 24 has a plurality of passageways 102 that extend through the flange 90. Each passageway 102 is configured to cooperate with a trochanteric reattachment device 162 (see FIG. 11) to couple the femoral prosthesis 12 in a fixed position relative to the trochanter 134 of the patient's femur 130. An example of a trochanteric reattachment device 162 may be the Trochanteric Reattachment Device produced and distributed by DePuy Synthes Products, Inc., of Raynham Mass. In the illustrative embodiment, the passageways 102 are sized to receive cables 166 of the trochanteric reattachment device 162. It should be appreciated that in other embodiments the trochanter collar 24 may include additional passageways or the passageways may be omitted.

Figure 6:
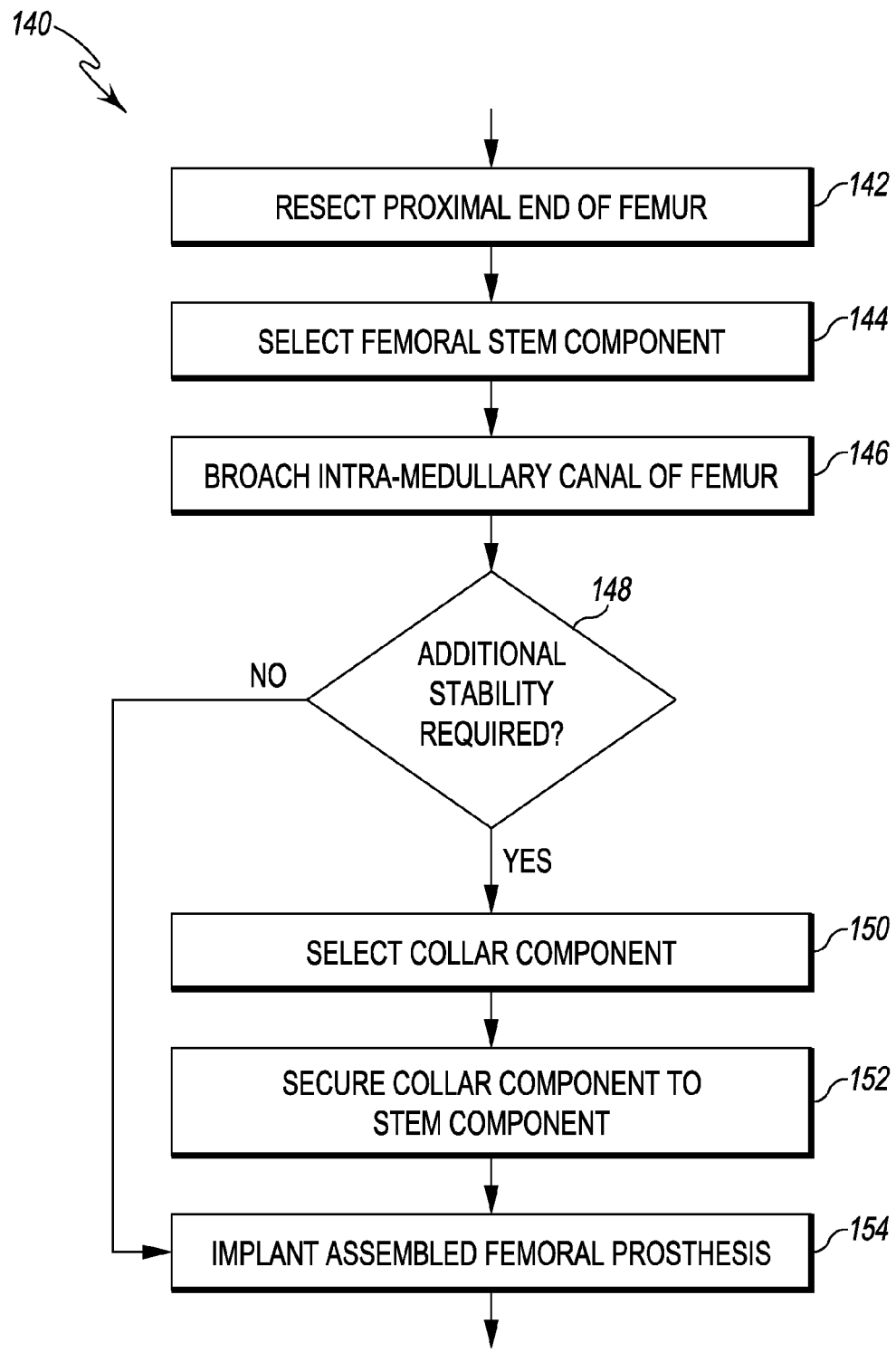
FIG. 6 a simplified block diagram of a method for implanting a femoral prosthesis assembly assembled from the femoral prosthesis system of FIG. 1.
Figure 8:
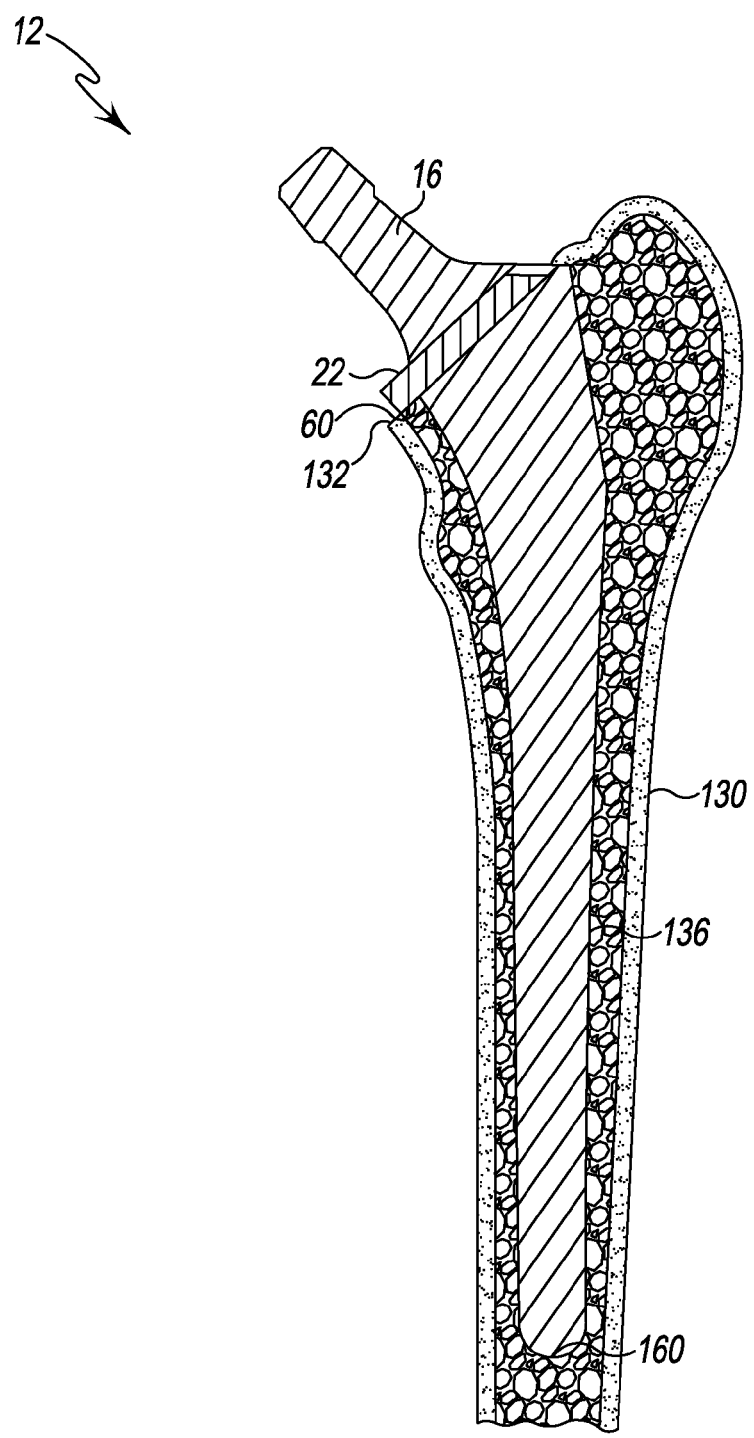
FIG. 8 is a partially cut-away view of the femoral prosthesis assembly of FIG. 7 implanted in a patient's femur.
Figure 9:
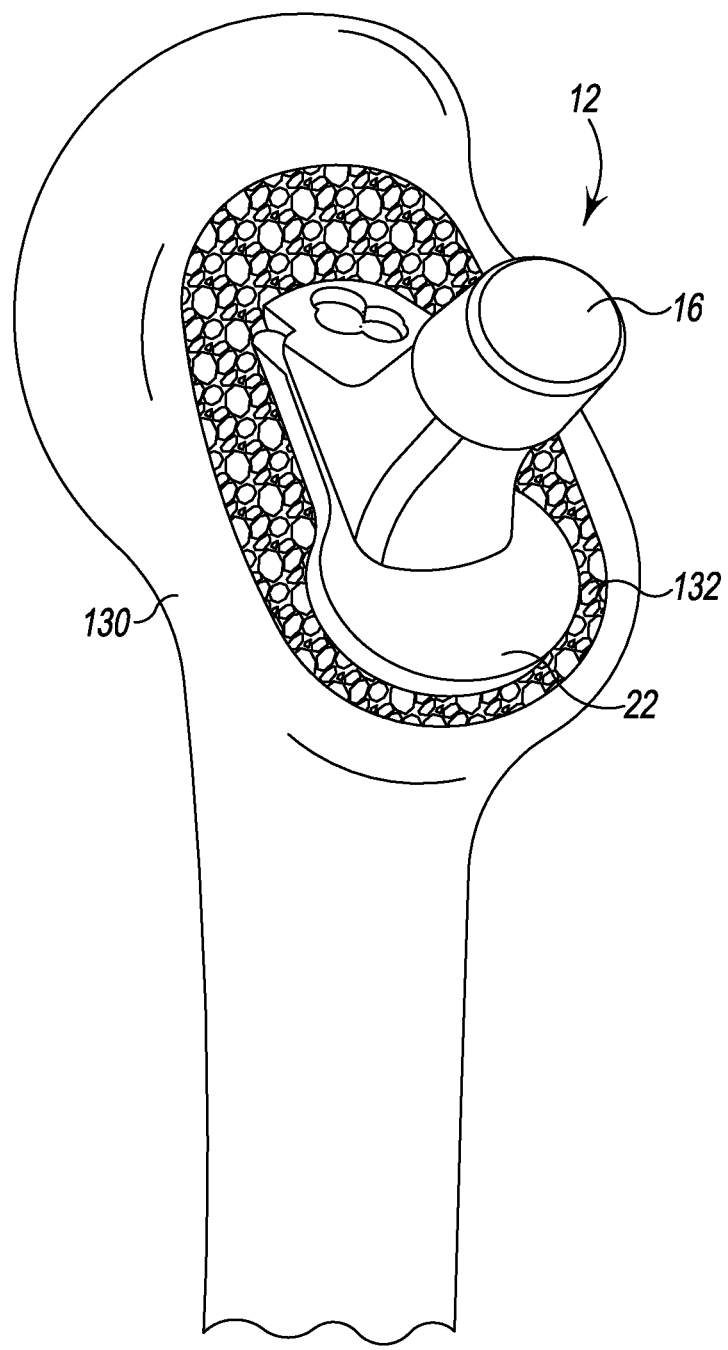
FIG. 9 is a perspective view of the assembled femoral prosthesis assembly of FIG. 7 implanted in a patient's femur.
Figure 11:
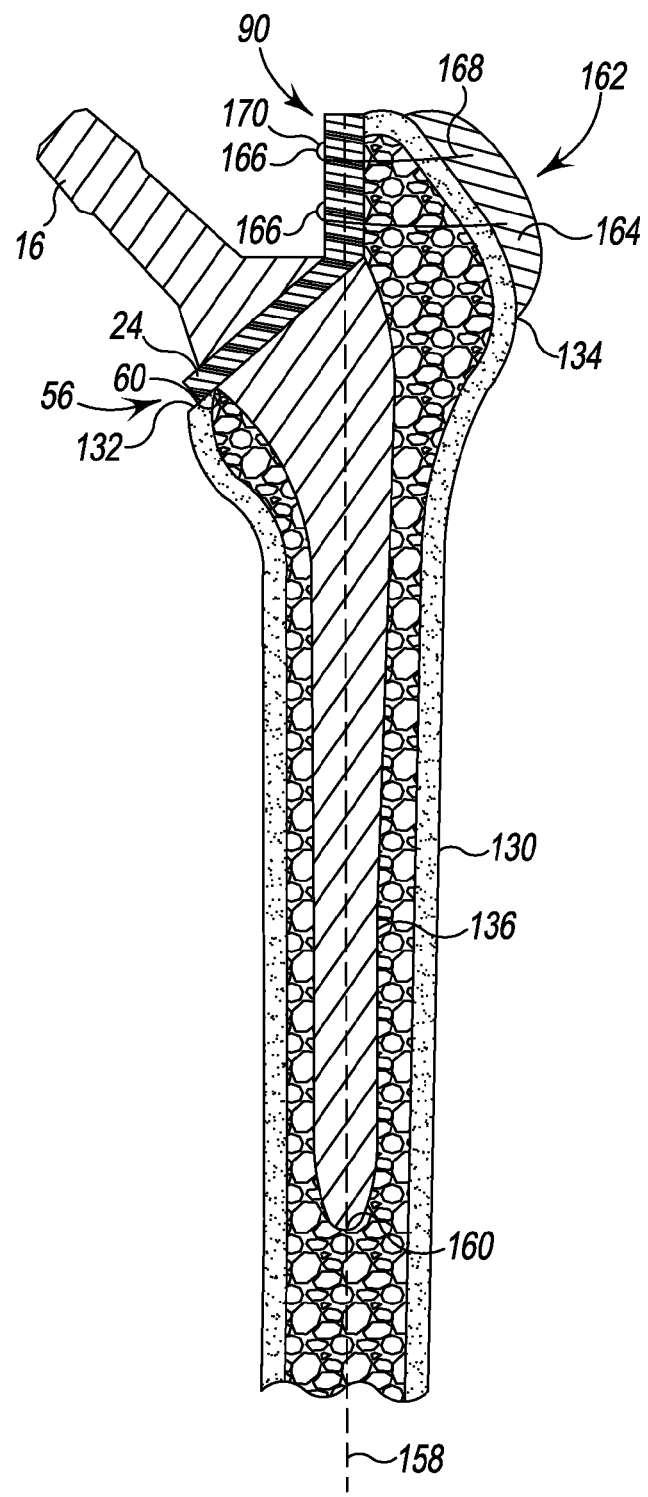
FIG. 11 is a partially cut-away view of the femoral prosthesis assembly of FIG. 10 implanted in a patient's femur.

Referring now to FIG. 6, a method 140 for performing a hip arthroplasty is shown. At block 142, an orthopaedic surgeon, or other member of a surgical team, may resect a proximal end of a patient's femur 130 to form a planar proximal surface 132 as shown in FIGS. 8 and 9. As described above, the femoral prosthesis 12 may include a stem component 16 and a femoral head component 18. Depending on the needs of the patient, the surgeon may also include the stabilizing collar 22 or trochanter collar 24 in the femoral prosthesis 12. In some embodiments, such as the case in some revision hip arthroplasties, an orthopaedic surgeon will also prepare medial surface of a trochanter 134 of the patient's femur 130, as shown in FIG. 11. At block 144, the orthopaedic surgeon selects a stem component 16 and a femoral head component 18 based on surgical parameters determined before the surgical operation began and intra-operative data determined during the surgical operation.

At block 146, the orthopaedic surgeon may insert a broach through the planar proximal surface 132 of the patient's femur to define a passageway 136 in the intramedullary canal of the patient's femur 130 sized to receive the selected femoral stem component 16. The passageway is shown in FIGS. 8 and 11. The size of the broach used by the orthopaedic surgeon is determined based on the size of the selected femoral component.

At block 148, the orthopaedic surgeon determines whether the femoral prosthesis 12 requires more stability than what is provided by the stem component 16 alone. If the femoral prosthesis 12 does not require additional stability, the surgeon may continue to block 154 in which the stem component 16 and the femoral head component 18 are implanted in the patient's femur 130. If additional stability is required, the surgeon continues to block 150 in which the surgeon selects a collar from the plurality of collars 14 to couple to the stem component 16. Each of the collars of the plurality of collars includes an inferior surface 60 configured to engage the planar proximal surface 132 of the patient's femur 130. The plurality of collars 14 may include a number of different types of collars configured to provide different types of stability. For example, the stabilizing collar 22 includes a platform that provides a large surface area to engage the planar proximal surface 132 of the patient's femur 130. In another example, the trochanter collar 24 includes a flange 90 configured to couple a trochanter 134 of the patient's femur 130 to the femoral prosthetic assembly.

Figure 7:
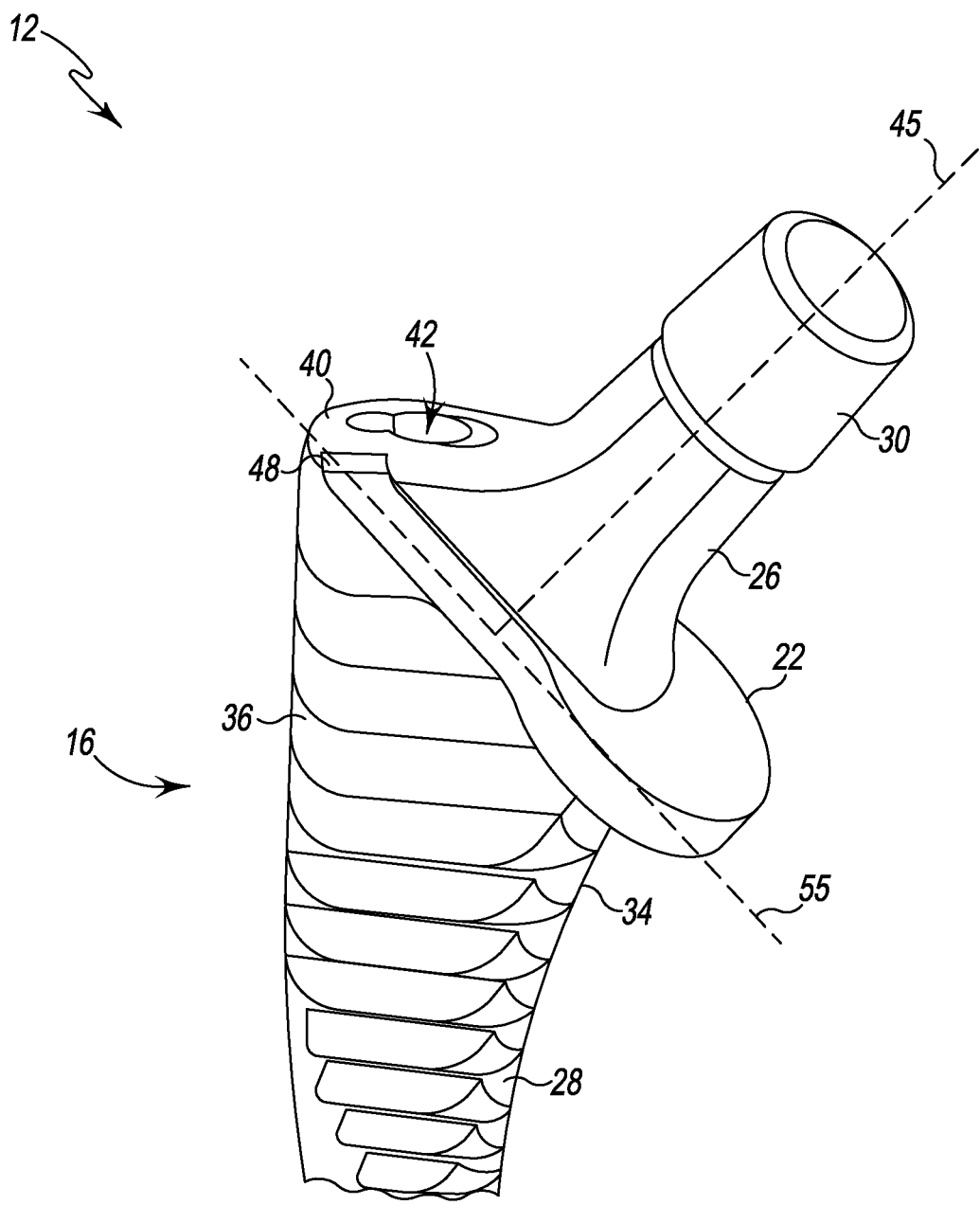
FIG. 7 is a perspective view of an embodiment of a femoral prosthesis assembly including one of the collars of FIG. 1 coupled to the stem component of FIG. 1.
Figure 10:
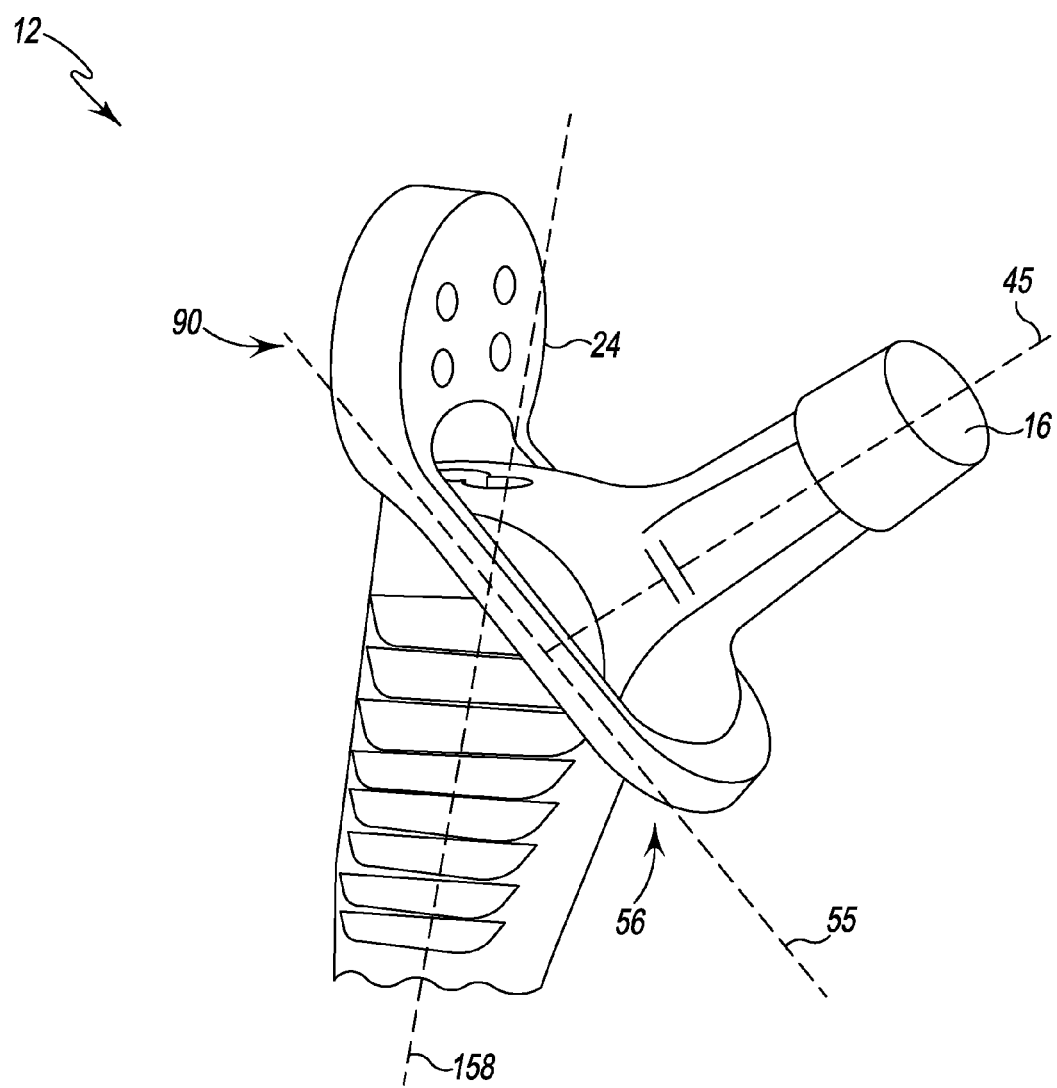
FIG. 10 is a perspective view of an embodiment of another femoral prosthesis assembly including another of the collars of FIG. 1 and coupled to the stem component of FIG. 1.

At block 152, the orthopaedic surgeon may secure the selected collar to the stem component 16 such that the inferior surface 60 of the collar extends transversely to the longitudinal axis 45 of the stem component 16 (See FIGS. 7 and 10). As will be discussed in more detail below, the plurality of collars 14 may be coupled to the stem component 16 in a variety of different ways.

At block 154, once the selected collar is secured in a fixed position relative to the stem component 16, the assembled femoral prosthesis 12 is positioned and implanted in the patient's femur 130 such that the inferior surface 60 of the selected collar engages with the planar proximal surface 132 of the patient's femur 130 (See FIGS. 8 and 11). The proper positioning of the femoral prosthesis 12 depends on the selected collar that has been coupled to the stem component 16. In some embodiments, such as in the case of the trochanter collar 24, additional steps are taken to secure the collar to other parts of the patient's femur 130.

As discussed above, each of the collar components 14 may be coupled to the stem component 16 in a number of different ways. As shown in FIG. 7, the illustrative stabilizing collar 22 is coupled to the stem component 16 by advancing the stabilizing collar 22 into the groove 44 of the stem component 16. The groove 44 includes two channels 50, 52, each having a longitudinal axis 55 that extends transversely to the longitudinal axis 45 of the trunnion 30. To couple the stabilizing collar 22 to the stem component 16, the lateral end 70 of the stabilizing collar 22 is advanced along the longitudinal axis 55 defined by the channels 50, 52. As the stabilizing collar 22 is advanced along the longitudinal axis 55, the stem component 16 passes through the opening 68 of the stabilizing collar 22 and into the slot 66 of the stabilizing collar 22. The groove 44 receives the plurality of arms 74, 76 of the stabilizing collar 22. The stabilizing collar 22 is advanced until the inner wall 64 of the stabilizing collar 22 engages the base walls 54 that define the groove 44 formed in the stem component 16. As discussed above, in the illustrative embodiment, the stabilizing collar 22 is coupled to the stem component 16 via a press-fit.

As shown in FIG. 8, once the stabilizing collar 22 is coupled to the stem component 16, the femoral prosthesis 12 is inserted into the broached intramedullary canal of the patient's femur 130. The femoral prosthesis 12 is positioned such that the inferior surface 60 of the stabilizing collar 22 contacts the surgically prepared proximal surface 132 of the patient's femur 130. In this way, the stabilizing collar 22 provides stability to the femoral prosthesis 12 while the patient's natural bone grows around the femoral prosthesis 12.

To couple the trochanter collar 24 to stem component 16, the distal tip 160 of the stem component 16 is inserted into the slot 66 of the trochanter collar 24. The trochanter collar is advanced proximally up the stem component 16 along a body axis 158 that extends along the elongated body 28 of the stem component 16. As shown in FIG. 10, the trochanter collar 24 is coupled to the stem component 16 by positioning the base 56 of the trochanter collar 24 in the groove 44 of the stem component 16. When so coupled, the inner wall 64 of the trochanter collar 24 engages the base walls 54 that define the groove 44 formed in the stem component 16.

As shown in FIG. 11, the femoral prosthesis 12 that includes the trochanter collar 24 is secured to the trochanter 134 of the patient's femur 130 using a trochanteric reattachment device 162. An embodiment of the trochanteric reattachment device 162 includes a body 164 configured to be coupled to the trochanter 134 of the patient's femur 130 and a plurality of cables 166 extending from the body 164. The cables 166 include a first end 168 secured to the body and a second end 170. The second end 170 of the cables 166 are threaded through the passageways 102 formed in the flange 90 of the trochanter collar 24. The second end 170 of the cables 166 are then secured to the body 164. In this way, the femoral prosthesis 12 is securely engaged with the trochanter 134 of the patient's femur 130.

In some embodiments, the groove 44 and the plurality of collars 14 may include complimentary features to couple the plurality of collars 14 to the stem component 16. For example, the groove 44 may include a flange that mates with a corresponding aperture formed in the plurality of collars 14, or vice versa. In other embodiments, the plurality of collars 14 may be coupled to the stem component 16 by a fastening device, such as a clip or a screw.

Referring now to FIGS. 12-19, another embodiment of a modular femoral prosthesis system (hereinafter system 210) of a hip prosthesis is shown. Some of the features of FIGS. 12-19 are similar to the features described in the embodiment shown in FIGS. 1-11. For such features, the reference numbers from the embodiment described above will be used to identify those features in FIGS. 12-19. Like the embodiment of FIGS. 1-11, the femoral prosthesis system 210 may be utilized to assemble a femoral prosthesis 212 customized to the needs of each patient.

The femoral prosthesis system 210 includes a femoral stem component 216 configured to be implanted into a patient's femur 130, the femoral head component 18 configured to be attached to the femoral stem component 216, and a plurality of modular collar components 214 configured to be separately and selectively secured to the femoral stem component 216. In use, an orthopaedic surgeon may assemble a femoral prosthesis 212 using the various components before implanting the assembled femoral prosthesis 212 in the patient's femur 130 (see FIGS. 18-19).

Figure 12:
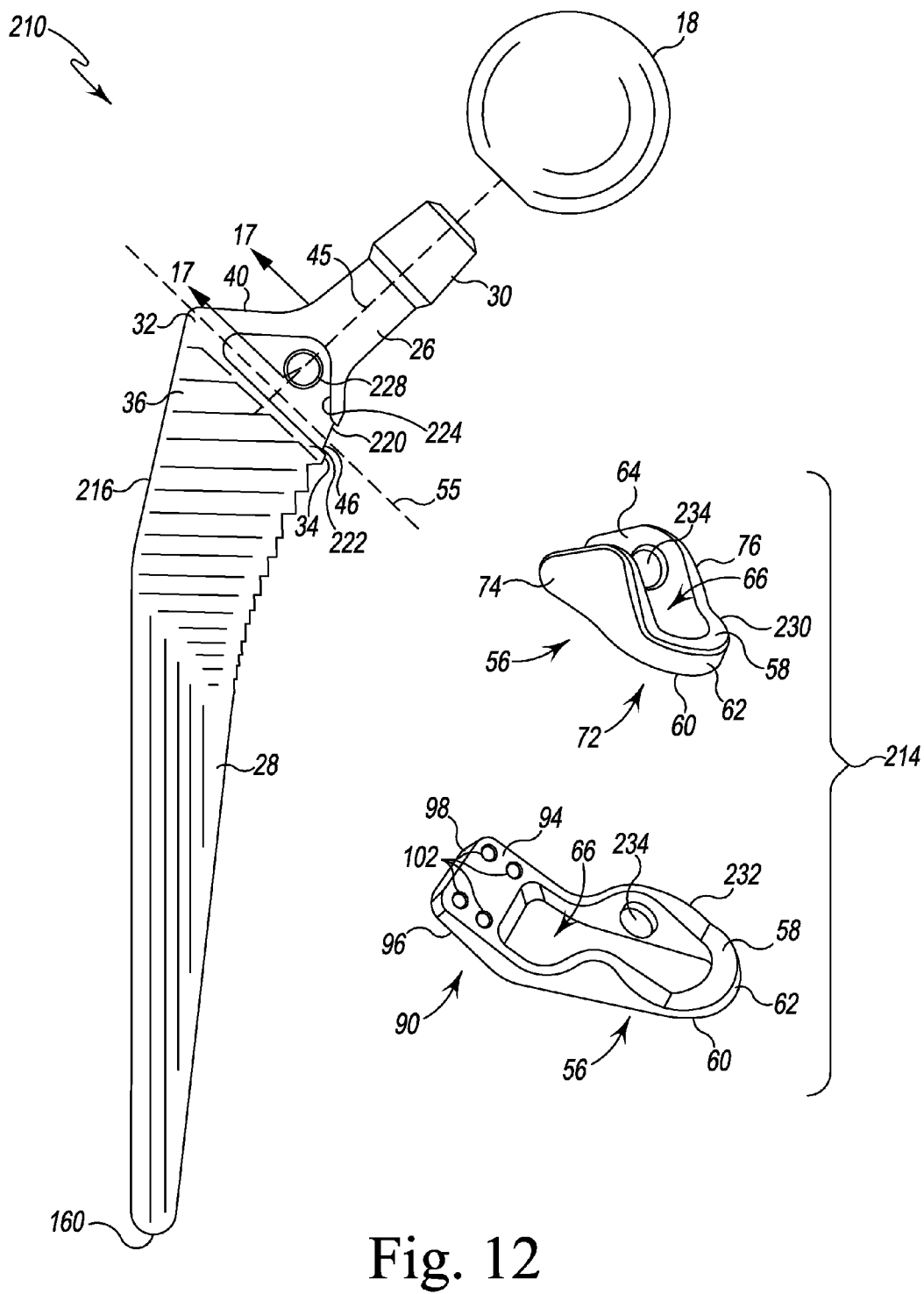
FIG. 12 is a perspective view of another embodiment of a femoral prosthesis system including a femoral stem component and a plurality of collars for use with the stem component.
Figure 13:
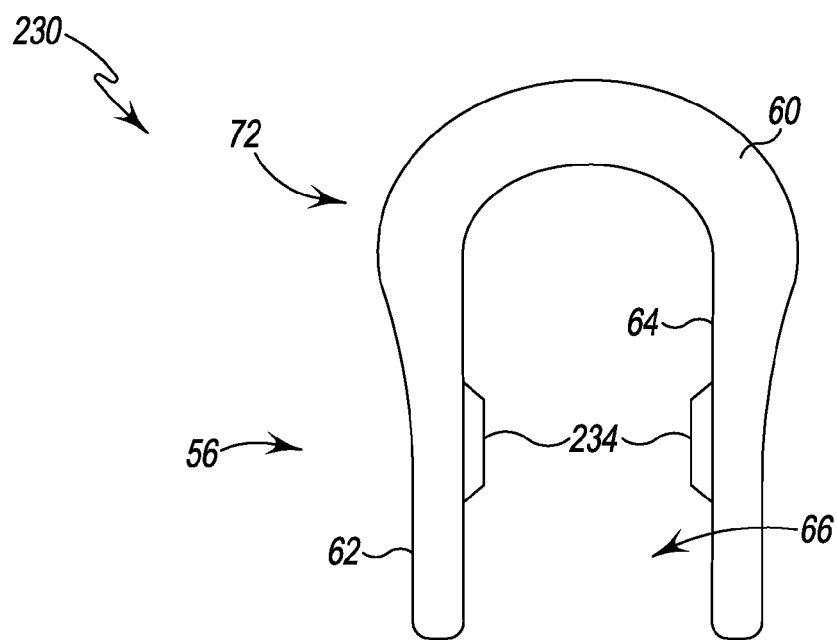
FIG. 13 is a bottom plan view of one of the collars of FIG. 12.
Figure 14:
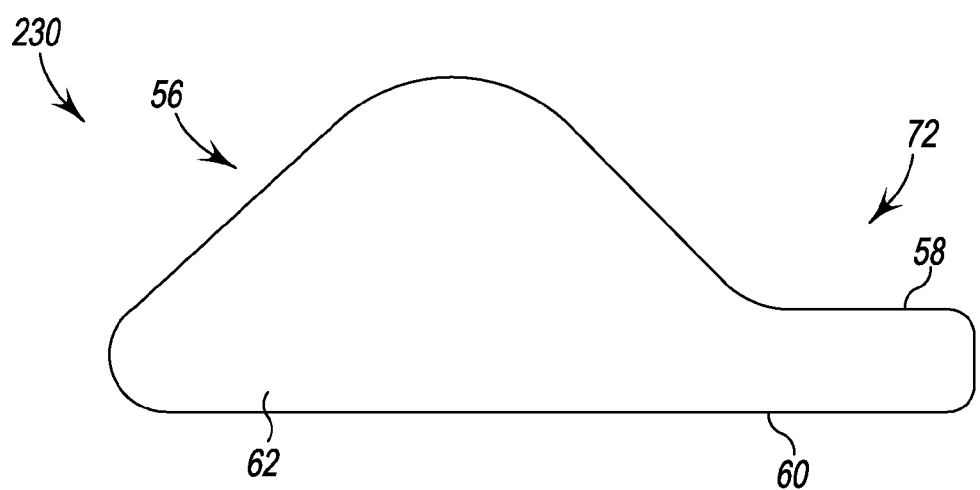
FIG. 14 is a side elevation view of the collar of FIG. 13.

As shown in FIG. 12, the stem component 216 includes the neck 26, the elongated body 28 configured to be received in a surgically-prepared cavity of the patient's femur 130, and the trunnion 30 extending superiorly and medially from the neck 26. The shoulder 32 connects the neck 26 to the elongated body 28 and is configured to be secured to one of the collar components 214. In the illustrative embodiment, the stem component 216 includes a groove 220 positioned in the shoulder 32 that is sized to receive portions of each collar component 214. The groove 220 is configured to secure the collar component 214 to the stem component 216 via a mechanical connection.

Figure 17:
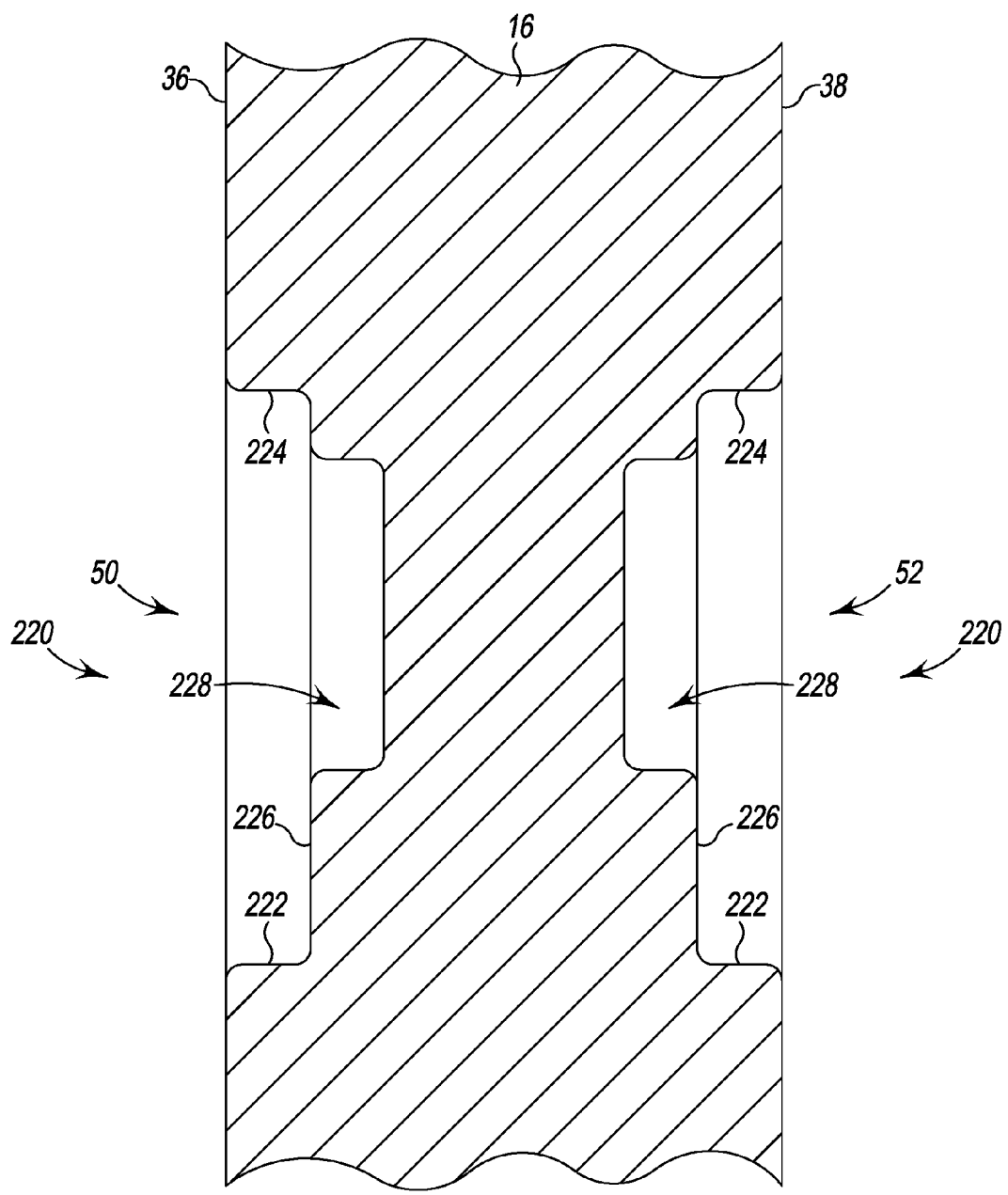
FIG. 17 is a cross-sectional view of the stem component of FIG. 12 taken along the line 15-15 in FIG. 12.
Figure 18:
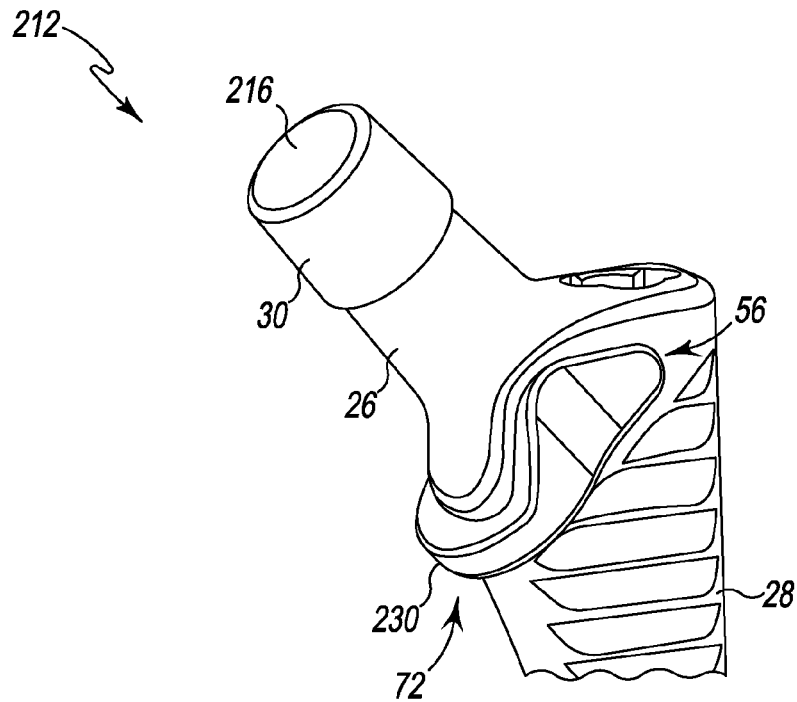
FIG. 18 is a perspective view of an embodiment of a femoral prosthesis assembly including one of the collars of FIG. 12 coupled to the stem component of FIG. 12.
Figure 19:
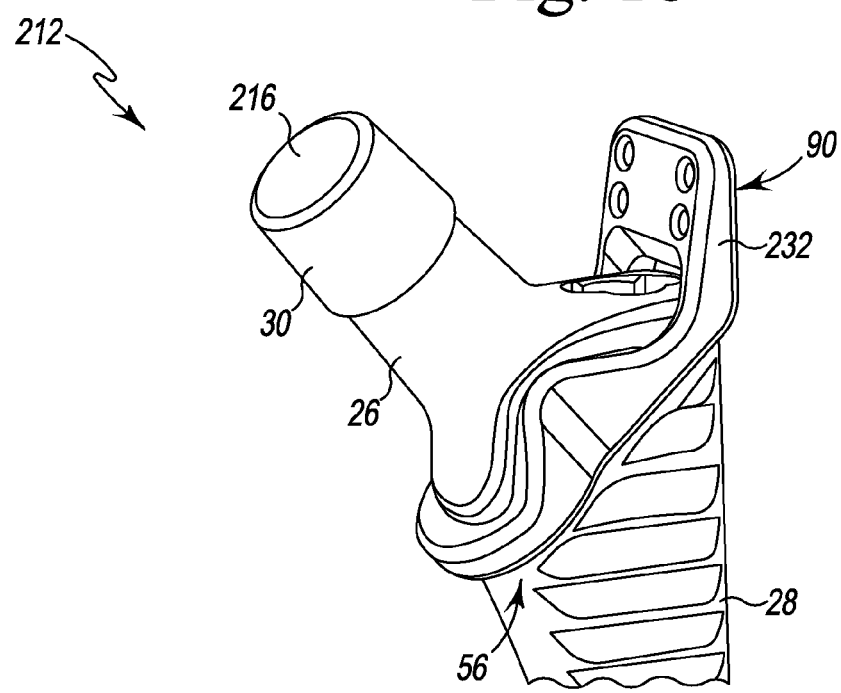
FIG. 19 is a perspective view of another embodiment of a femoral prosthesis assembly including another of the collars of FIG. 12 coupled to the stem component of FIG. 12.

As shown in FIGS. 12 and 17, the groove 220 includes a pair of channels 50, 52 that are defined in the anterior surface 36 and the posterior surface 38, respectively, of the shoulder 32. The channels 50, 52 extend from open ends 46 defined in the medial surface 34 of the shoulder 32. Each channel 50, 52 extends along the longitudinal axis 55 that extends transversely to the longitudinal axis 45 of the trunnion 30. As shown in FIG. 17, each of the channels 50, 52 is defined by base walls 54 that extend inwardly from openings defined the surfaces 36, 38. The base walls 54 include a planar bottom surface 222 that extends transversely to the longitudinal axis 45 of the trunnion 30, a curved top surface 224, and a base surface 226 extending between the planar bottom surface 222 and the curved top surface 224.

Each channel 50, 52 includes an aperture 228 formed in the base surface 226 and configured to receive a corresponding protrusion 234 formed on each of the collar components 214, as described in greater detail below. In the illustrative embodiment, the aperture 228 does not extend through the stem component 216. In other embodiments, however, the aperture 228 extends from the base surface 226 of channel 50 to the base surface 226 of channel 52.

As shown in FIG. 12, the system 210 includes a stabilizing collar 230 and a trochanter collar 232 that are configured to be selectively coupled to the stem component 216. In the illustrative embodiment, each of the collars 230, 232 is configured to engage a surgically prepared proximal surface 132 of the patient's femur 130 when the femoral prosthesis 212 is positioned in the patient's femur 130.

In the illustrative embodiment, each of the collars 230, 232 includes a base 56 that is configured to engage with the stem component 216. Similar to the collars described above, the base 56 of each collar 230, 232 includes the superior surface 58, the inferior surface 60, the outer surface 62, and the inner wall 64 that defines the slot 66.

Each base 56 also includes a pair of protrusions 234 are formed on the inner wall 64 of the base 56. The protrusions 234 are configured to act as retainers to mechanically secure each collar component 214 to the stem component 216. The protrusions 234 may be used in addition to the press-fit connection between the collar components and the stem component described above. In other embodiments, however, the protrusions 234 may be used on their own to couple the collar components 214 to the stem component 216.

The protrusions 234 are sized to be received into the apertures 228 formed in the base surfaces 226 of each channel 50, 52. The protrusions 234 are positioned such that when a collar component 214 is coupled securely to the stem component 216, the protrusions 234 are received into the each aperture 228. A portion of the superior surface 58 of the base 56 extends superiorly away from the inferior surface 60 of the base 56 to form the structure that supports the protrusions 234. Each protrusion 234 extends inwardly from the inner wall 64.

Figure 15:
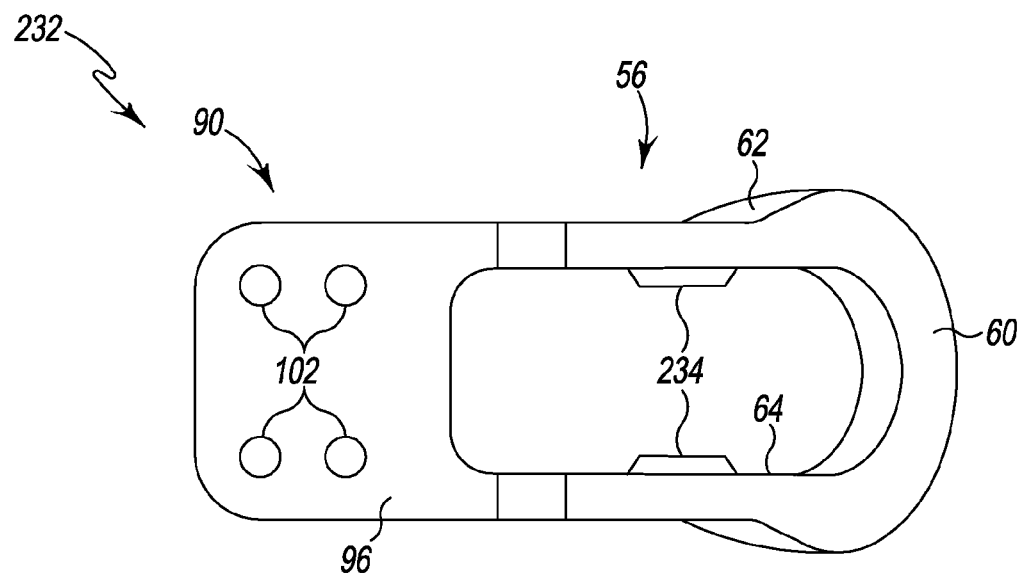
FIG. 15 is a bottom plan view of another of the collars of FIG. 12.
Figure 16:
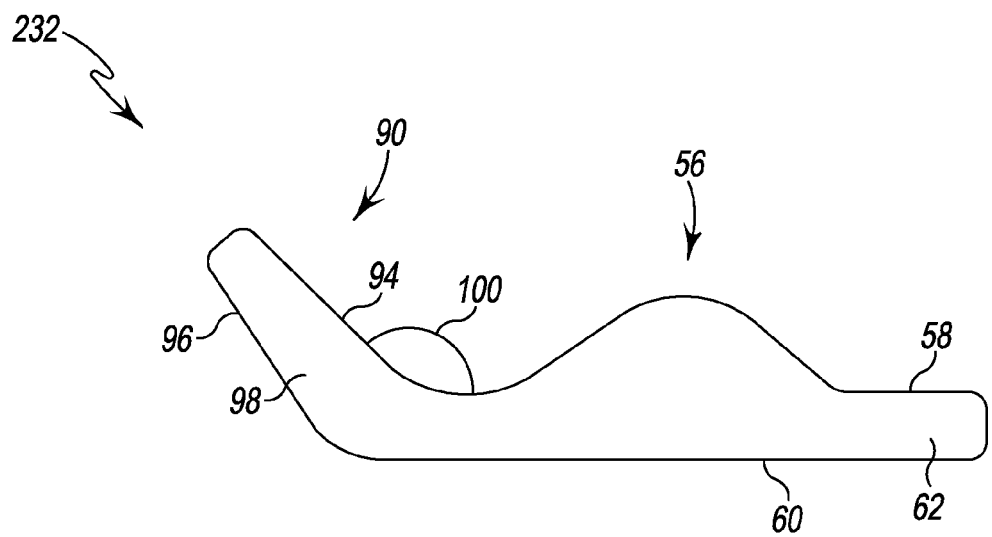
FIG. 16 is a side elevation view of the collar of FIG. 15.

As shown in FIGS. 15-16, the illustrative slot 66 of the trochanter collar 232 is surrounded by the inner wall 64 such that the slot 66 is a closed slot. The trochanter collar 232 includes the base 56 and the flange 90 extending away from the lateral end 92 of the base 56.

The femoral prosthesis 212 may be assembled in the manner described above. For example, the stabilizing collar 230 may be advanced along the longitudinal axis 55 such that the pair of arms 74, 76 of the stabilizing collar 230 are received into the groove 220. The stabilizing collar 230 is advanced until the pair of protrusions 234 are received into each aperture 228 formed in the groove 220.

Figure 20:
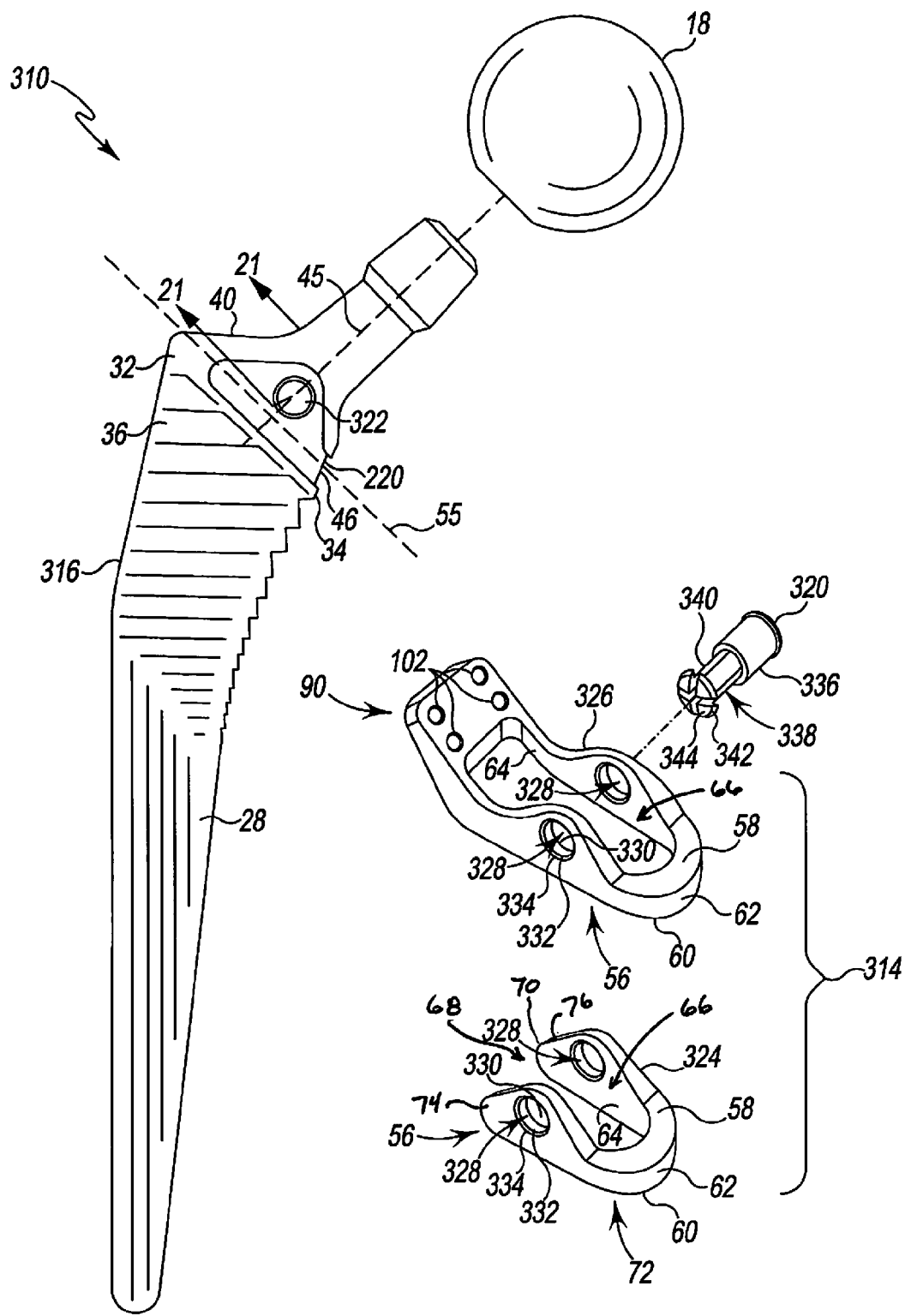
FIG. 20 is a perspective view of another embodiment of a femoral prosthesis system including a femoral stem component, a plurality of collars for use with the stem component, and a fastener.
Figure 21:
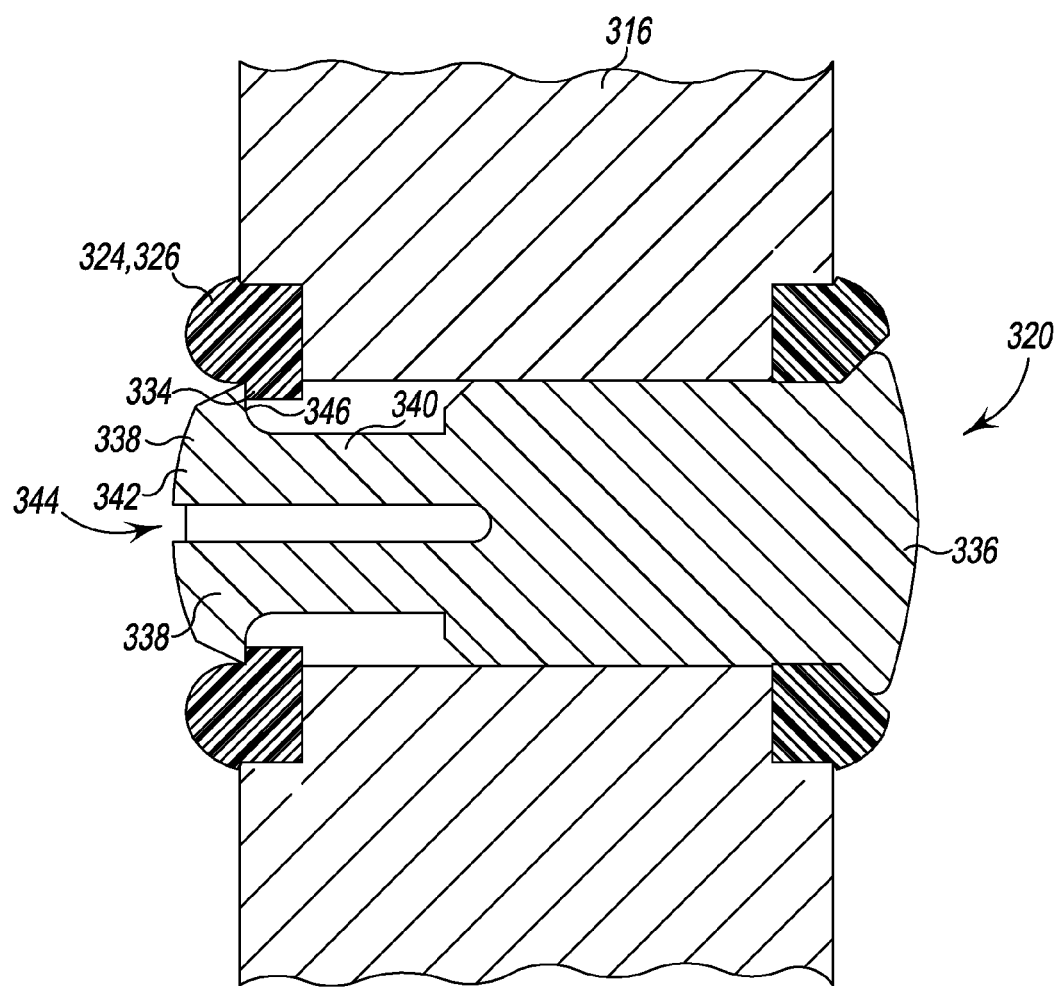
FIG. 21 is a cross-sectional view of a femoral prosthesis assembly including the stem component of FIG. 20, one of the collars of FIG. 20, and the fastener of FIG. 20 taken along the line 21-21 in FIG. 20.

Referring now to FIGS. 20-21, another embodiment of a modular femoral prosthesis system (hereinafter system 310) of a hip prosthesis is shown. Some of the features of FIGS. 20-21 are similar to the features described in the embodiments shown in FIGS. 1-19. For such features, the reference numbers from the embodiments described above will be used to identify those features in FIGS. 20-21. Like the embodiments of FIGS. 1-19, the femoral prosthesis system 310 may be utilized to assemble a femoral prosthesis 312 customized to the needs of each patient.

The femoral prosthesis system 310 includes a femoral stem component 316 configured to be implanted into a patient's femur 130, the femoral head component 18 configured to be attached to the femoral stem component 316, a plurality of modular collar components 314 configured to be separately and selectively secured to the femoral stem component 316, and a fastener 320 configured to secure a collar component 314 to the stem component 316. In use, an orthopaedic surgeon may assemble a femoral prosthesis 312 using the various components before implanting the assembled femoral prosthesis 312 in the patient's femur 130.

As shown in FIG. 20, the stem component 316 includes the neck 26, the elongated body 28 configured to be received in a surgically-prepared cavity of the patient's femur 130, and the trunnion 30 extending superiorly and medially from the neck 26. The shoulder 32 connects the neck 26 to the elongated body 28. In the illustrative embodiment, the stem component 316 includes the groove 220 that is sized to receive portions of each collar component 314 to secure the collar component 314 to the stem component 316 via the fastener 320.

As shown in FIG. 21, an aperture 322 extends through stem component 316 between the base walls 54 of each channel 50, 52. The aperture 322 is configured to receive the fastener 320 and secure one of the collar components 314 to stem component 316. The aperture 322 is configured to align with through-holes 328 formed in the base 56 of the collar components 314.

As shown in FIG. 20, the system 310 includes a stabilizing collar 324 and a trochanter collar 326 that are configured to be selectively coupled to the stem component 316. In the illustrative embodiment, each of the collars 324, 326 is configured to engage a surgically prepared proximal surface 132 of the patient's femur 130 when the femoral prosthesis 312 is positioned in the patient's femur 130. Each of the collars 324, 326 includes a base 56 that is configured to engage with the stem component 316. The base 56 includes the superior surface 58, the inferior surface 60, the outer surface 62, and the inner wall 64 that defines the slot 66 in each of the collars 324, 326. The stabilizing collar 324 has an opening 68 formed at a lateral end 70 of its base 56. The base 56 of the stabilizing collar 324 also includes a platform 72 that is positioned opposite the opening 68 and a pair of arms 74, 76 that extend laterally from the platform 72 along the slot 66.

A pair of through-holes 328 sized to receive the fastener 320 are formed in the base 56. Each of the through-holes 328 extend from a first opening 330 formed in the inner wall 64 of the base 56 to a second opening 332 formed in outer surface 62 of the base 56. One of the through-holes 328 of each collar component 314 include a lip surface 334 configured to engage with a corresponding flange surface on the fastener 320. The pair of through-holes 328 are positioned on the base 56 such that when the collar component 314 is coupled to the stem component 316, the pair of through-holes 328 align with the aperture 322. A portion of the superior surface 58 of the base 56 extends superiorly away from the inferior surface 60 of the base 56 to form the structure that defines the through-holes 328.

The fastener 320 includes a fastener head 336 and a plurality of cantilevered arms 338 extending distally away from the fastener head 336. In other embodiments, however, the cantilevered arms may not always be present. For example, the fastener 320 may include ridges that are received into corresponding threads formed in the collar components 314 and the stem component 316. Each of the cantilevered arms 338 include an arm body 340 and a flange 342 positioned at a distal end 344 of each arm body 340. Each flange 342 includes a flange surface 346 configured to engage with the lip surface 334 of each collar component 314. The cantilevered arms 338 are configured to be deflected when the fastener 320 is used to secure a collar component 314 to the stem component 316. In the illustrative embodiment, the fastener 320 is formed from an implantable metallic material such as, for example, stainless steel, cobalt chromium, or titanium. In other embodiments, however, the fastener 320 may be made of a polymeric material.

As discussed above, the fastener 320 is configured to secure one of the collar components 314 to the femoral stem component 316. In use, a collar component 314 is selected from the plurality of collar components 314 to secure to the femoral stem component 316. The selected collar component 314 is positioned on the femoral stem component 316 such that the through-holes 328 of the selected collar component 314 align with the aperture 322 formed in the stem component 316. Once aligned, the fastener 320 is advanced through the through-holes 328 and the aperture 322 to secure the selected collar component 314 in a fixed position relative to the stem component 316. As the fastener 320 passes through the first through-hole 328, the cantilevered arms 338 of the fastener 320 are deflected inwardly. After the flange 342 of each cantilevered arm 338 passes through the second through-hole 328 of the selected collar component 314, each cantilevered arm 338 expands outwardly to engage the lip surface 334 of the selected collar component 314. Specifically, the flange surface 346 of each cantilevered arm 338 engages the lip surface 334 to secure the selected collar component 314 to the stem component 316.

Figure 22:
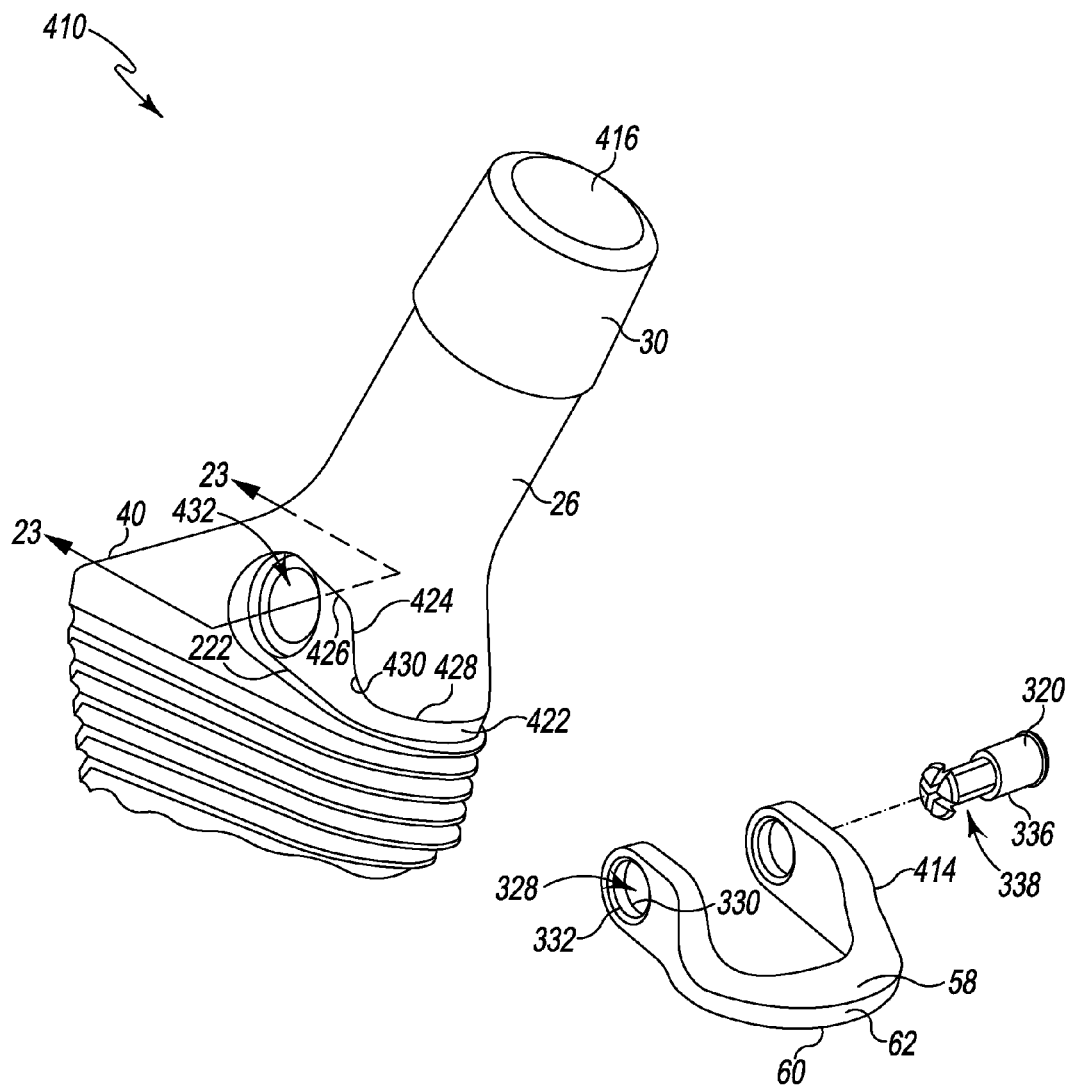
FIG. 22 is a perspective view of another embodiment of a femoral prosthesis system including a femoral stem component, a collar for use with the stem component, and a fastener.
Figure 23:
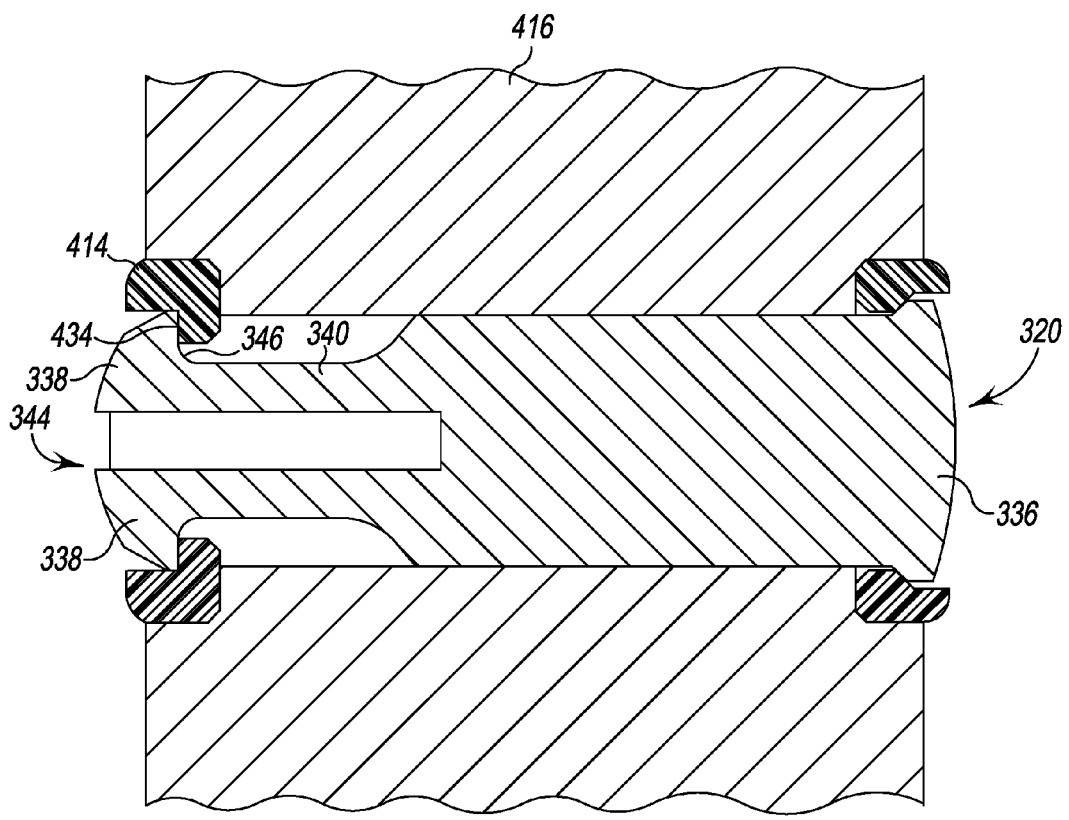
FIG. 23 is a cross-sectional view a femoral prosthesis assembly including the stem component of FIG. 22, the collar of FIG. 22, and the fastener of FIG. 22 taken along the line 23-23 in FIG. 22.
Figure 24:
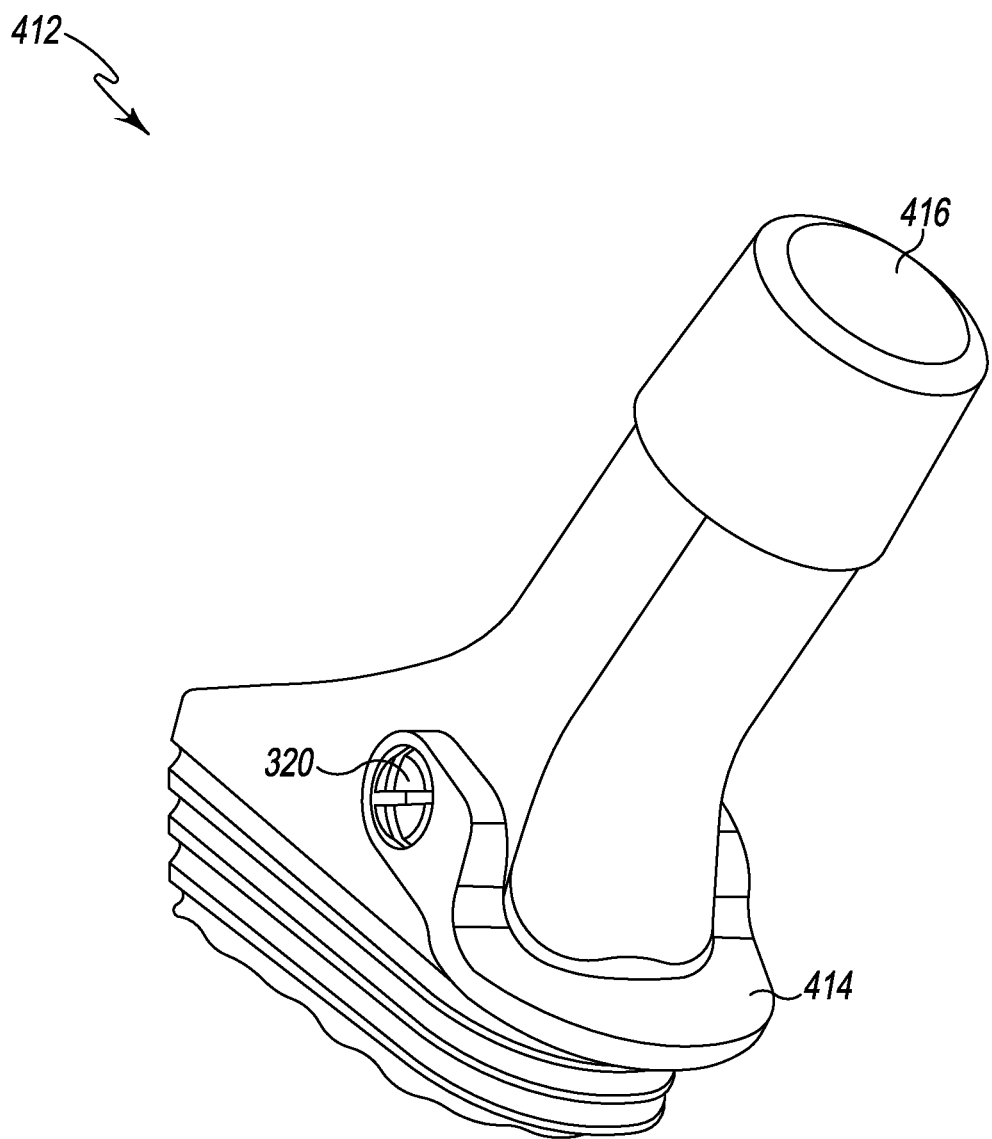
FIG. 24 is a perspective view of the femoral prosthesis assembly of FIG. 23.

Referring now to FIGS. 22-24, another embodiment of a modular femoral prosthesis system (hereinafter system 410) of a hip prosthesis is shown. Some of the features of FIGS. 22-24 are similar to the features described in the embodiments shown in FIGS. 1-21. For such features, the reference numbers from the embodiments described above will be used to identify those features in FIGS. 22-24. Like the embodiments of FIGS. 1-21, the femoral prosthesis system 410 may be utilized to assemble a femoral prosthesis 412 customized to the needs of each patient.

The femoral prosthesis system 410 includes a femoral stem component 416 configured to be implanted into a patient's femur 130, the femoral head component 18 configured to be attached to the femoral stem component 416, a collar component 414 configured to be selectively secured to the femoral stem component 416, and the fastener 320 configured to secure a collar component 414 to the stem component 416. In use, an orthopaedic surgeon may assemble a femoral prosthesis 412 using the various components before implanting the assembled femoral prosthesis 412 in the patient's femur 130.

The stem component 416 includes a groove 422 formed in the shoulder 32 of the stem component 416. The groove 422 is sized to receive portions the collar component 414 and to secure the collar component 414 to the stem component 416 via the fastener 320. The groove 422 includes the pair of channels 50, 52 that are defined in the anterior surface 36 and the posterior surface 38, respectively, of the shoulder 32. The channels 50, 52 extend from open ends 46 defined in the medial surface 34 of the shoulder 32. Each of the channels 50, 52 extends along the longitudinal axis 55 that extends transverse to the longitudinal axis 45 of the trunnion 30.

The channels 50, 52 are defined by base walls 54 that extend inwardly from openings defined the surfaces 36, 38. The base walls 54 include the planar bottom surface 222 that extends transversely to the longitudinal axis 45 of the trunnion 30, a top surface 424, and the base surface 226 extending between the planar bottom surface 222 and the top surface 424. The top surface 424 includes a first planar portion 426, a second planar portion 428, and a curved portion 430 extending therebetween.

An aperture 432 is formed in the base surface 226 of each of the channels 50, 52. As shown in FIG. 23, the aperture 432 extends through the stem component 416 and is configured to align with the through-holes 328 formed in the collar component 414.

The collar component 414 is configured to engage a surgically prepared proximal surface 132 of the patient's femur 130 when the femoral prosthesis 412 is positioned in the patient's femur 130. The collar component 414 may be formed from a rigid polymer such as polyetheretherketone (PEEK). In the illustrative embodiment, the collar component 414 includes a base 56 that is configured to engage with the stem component 216. The base 56 includes the superior surface 58, the inferior surface 60, the outer surface 62, and the inner wall 64 that defines the slot 66. The collar component 314 also includes a lip surface 434 configured to engage the flange surface 346 of the fastener 320.

As discussed above, the fastener 320 is configured to secure the collar component 414 to the femoral stem component 416. The collar component 414 is positioned on the femoral stem component 416 such that the through-holes 328 of the collar component 414 align with the aperture 432 formed in the stem component 416. Once aligned, the fastener 320 is advanced through the through-holes 328 and the aperture 432 to secure the collar component 414 in a fixed position relative to the stem component 416. As the fastener 320 passes through the first through-hole 328, the cantilevered arms 338 of the fastener 320 are deflected inwardly. After the flange 342 of each cantilevered arm 338 passes through the second through-hole 328 of the selected collar component 314, each cantilevered arm 338 expands outwardly to engage the lip surface 434 of the collar component 414. Specifically, the flange surface 346 of each cantilevered arm 338 engages the lip surface 434 to secure the collar component 414 to the stem component 416.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It should be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A modular femoral prosthesis system comprising:
a stem component configured to be received in a proximal end of a patient's surgically prepared femur, the stem comprising a neck, an elongated body extending distally from the neck, and a trunnion configured to receive a femoral head component extending medially and proximally from the neck, and
a plurality of collar components configured to be selectively coupled to the stem component in a fixed position adjacent to the neck of the stem component, each of the plurality of collar components including a base having an inferior surface configured to contact a surgically prepared proximal surface of the patient's femur, the plurality of collar components including:
a first collar component including the base, the base of the first collar component having (i) a platform and (ii) a pair of arms extending away from a lateral end of the platform, and
a second collar component including (i) the base and (ii) a flange extending away from a lateral end of the base, the flange being configured to secure the second collar component in a fixed position relative to a trochanter of the patient,
wherein the base includes a superior surface extending between a medial end of the base and the lateral end of the base and an inner wall extending between a first opening formed in the superior surface and a second opening formed in the inferior surface to define a slot sized to receive the stem component,
wherein the flange includes a medial surface that extends away from the superior surface of the base and cooperates with the base to define a non-orthogonal angle relative to the superior surface of the base, and the flange is configured to couple the stem component in a fixed position relative to the patient's trochanter,
wherein the trunnion defines a longitudinal axis that extends through the neck of the stem component, the stem component further comprises a shoulder positioned between the elongated body and the neck, and each collar component is configured to be coupled to the shoulder such that the inferior surface of the base of each collar component extends transverse to the longitudinal axis defined by the trunnion, and
wherein the shoulder includes an anterior surface, a posterior surface positioned opposite the anterior surface, and a medial surface positioned inferior of the neck and extending between the anterior and posterior surface, and a groove defined in the anterior surface, the posterior surface, and the medial surface of the shoulder, the groove extending transverse to the longitudinal axis of the trunnion and being configured to receive the base of each collar component to secure each collar component to the stem component.

2. The system of claim 1, wherein each collar component is made of a material different than the stem component.

3. The system of claim 2, wherein the stem component is made of a metallic material and each collar component is made of a biocompatible polymeric material.

4. The system of claim 3, wherein the biocompatible polymeric material is polyether ether ketone (PEEK).

5. The system of claim 1, wherein when the first collar component is coupled to the stem component, each of the pair of arms is received into the groove defined in the shoulder of the stem component.

6. The system of claim 1, wherein when the second collar component is coupled to the stem component an inner surface of the base is received into the groove defined in the shoulder of the stem component.

7. The system of claim 1, wherein:
the groove includes an anterior channel extending along the anterior surface of the shoulder and a posterior channel extending along the posterior surface of the shoulder, and
each channel extends from a first open end defined in the medial surface of the shoulder to a second open end defined in a superior, lateral surface of the shoulder.

8. The system of claim 7, wherein a socket sized to receive an insertion tool is defined in the superior, lateral surface of the shoulder.

9. A modular femoral prosthesis system comprising:
a stem component configured to be received in a proximal end of a patient's surgically prepared femur, the stem comprising a neck, an elongated body extending distally from the neck, and a trunnion configured to receive a femoral head component extending medially and proximally from the neck, and
a plurality of collar components configured to be selectively coupled to the stem component in a fixed position adjacent to the neck of the stem component, each of the plurality of collar components including a base having an inferior surface configured to contact a surgically prepared proximal surface of the patient's femur, the plurality of collar components including:
a first collar component including the base, the base of the first collar component having (i) a platform and (ii) a pair of arms extending away from a lateral end of the platform, and
a second collar component including (i) the base and (ii) a flange extending away from a lateral end of the base, the flange being configured to secure the second collar component in a fixed position relative to a trochanter of the patient,
wherein the base includes a superior surface extending between a medial end of the base and the lateral end of the base and an inner wall extending between a first opening formed in the superior surface and a second opening formed in the inferior surface to define a slot sized to receive the stem component,
wherein the flange forms a non-orthogonal angle with the superior surface of the base, and the flange is configured to couple the stem component in a fixed position relative to the patient's trochanter,
wherein the trunnion defines a longitudinal axis that extends through the neck of the stem component, the stem component further comprises a shoulder positioned between the elongated body and the neck, and each collar component is configured to be coupled to the shoulder such that the inferior surface of the base of each collar component extends transverse to the longitudinal axis defined by the trunnion, and wherein the shoulder includes:

an anterior surface, a posterior surface positioned opposite the anterior surface, and a medial surface positioned inferior of the neck and extending between the anterior and posterior surface, a groove defined in the anterior surface, the posterior surface, and the medial surface of the shoulder, the groove extending transverse to the longitudinal axis of the trunnion and being configured to receive the base of each collar component to secure each collar component to the stem component.

10. The system of claim 9, wherein when the first collar component is coupled to the stem component, each of the pair of arms is received into the groove defined in the shoulder of the stem component.

11. The system of claim 9, wherein when the second collar component is coupled to the stem component an inner surface of the base is received into the groove defined in the shoulder of the stem component.

12. The system of claim 9, wherein:

the groove includes an anterior channel extending along the anterior surface of the shoulder and a posterior channel extending along the posterior surface of the shoulder, and each channel extends from a first open end defined in the medial surface of the shoulder to a second open end defined in a superior, lateral surface of the shoulder.

13. The system of claim 12, wherein a socket sized to receive an insertion tool is defined in the superior, lateral surface of the shoulder.

14. The system of claim 9, wherein each collar component is made of a material different than the stem component.

15. The system of claim 9, wherein the stem component is made of a metallic material and each collar component is made of a biocompatible polymeric material.

16. The system of claim 15, wherein the biocompatible polymeric material is polyether ether ketone (PEEK).

* * * * *